(12) United States Patent
Cai et al.

(10) Patent No.: US 7,645,758 B2
(45) Date of Patent: *Jan. 12, 2010

(54) HETEROCYCLIC COMPOUNDS

(75) Inventors: Hui Cai, San Diego, CA (US); Nicholas I. Carruthers, Poway, CA (US); Curt A. Dvorak, San Diego, CA (US); James P. Edwards, San Diego, CA (US); Annette K. Kwok, Concord, NH (US); Jianmei Wei, San Diego, CA (US)

(73) Assignee: Janssen Pharmaceutica, N.V., Beerse (BE)

( * ) Notice: Subject to any disclaimer, the term of this patent is extended or adjusted under 35 U.S.C. 154(b) by 111 days.

This patent is subject to a terminal disclaimer.

(21) Appl. No.: 11/735,306

(22) Filed: Apr. 13, 2007

(65) Prior Publication Data

US 2007/0185120 A1 Aug. 9, 2007

Related U.S. Application Data

(63) Continuation of application No. 10/656,059, filed on Sep. 5, 2003, now Pat. No. 7,226,938.

(60) Provisional application No. 60/408,723, filed on Sep. 6, 2002.

(51) Int. Cl.
*C07D 241/04* (2006.01)
*A61K 31/497* (2006.01)
*C07D 403/00* (2006.01)

(52) U.S. Cl. .................................. 514/252.12; 544/358

(58) Field of Classification Search ............ 514/252.12; 544/358

See application file for complete search history.

(56) References Cited

U.S. PATENT DOCUMENTS 7,226,938 B2 * 6/2007 Cai et al. ..................... 514/359

FOREIGN PATENT DOCUMENTS

| EP | 0 180 500 | 5/1986 |
|---|---|---|
| EP | 0 282 133 | 9/1988 |
| EP | 1088824 A3 | 6/2001 |
| EP | 1136071 A2 | 9/2001 |
| WO | WO 9940914 | 8/1999 |
| WO | WO 02/072548 | 9/2002 |

OTHER PUBLICATIONS

Wolff, M.E., "Burger's Medicinal Chemistry", 5th Ed., Part 1, pp. 975-977 (1995).*
Banker et al., "Modern Pharmaceuticals", 3rd Ed., p. 596 (1996).*
Detty, M.R. et al. Studies Toward Alkylthiophene-2-Carboxaldehydes. Reduction of 3-Alkenythiophenes with Triathylsilane/Trifluoroacetic Acid. Regioselectivity in Formylation Reactions of 3-Alkythiophens. Haterocycles (1995) 40(2);925-937.

Kondo, K. et al. Synthetic Utility of tart-Butyl Azicloacetate on the Hemetsberger-Knittel Reaction (Synthelic Studies of indoles and Related Compounds Part 47). Chem. Pharm. Bull. (1999) 47(9):1227-1231.
Iriarte, J. et al. The Chlorination of Thiophene-2-aidehyde and Ethyl Thiophene-2-carboxylate in the Presence of Excess Aluminum Chloride. J. Het. Chem. (1976) 13:393-394.
Arrang, J.-M. et al. Auto-inhibition of Brain Histamine Release Mediated by a Novel Class (H3) of Histamine Receptor, Nature (1983) 302:832-837.
Ash, A.S.F.; Schild, H.D. Receptors Mediating Some Actions of Histamine. Br. J. Pharmac. Chemolher, (1966) 27:427-439.
Barger. G.; Dale, H.H. Chemical Structure and Sympathomimetic Action of Amines. J. Physiol. (1910) 41:19-59 Reprinted in Adventures in Physiology; Sir Henry H. Dale, Ed.; The Wellcome Trust: London, 1965; pp. 67-98.
Black J.W. et al. Definition and Antagonism of Histamine H2-Receptors. Nature (1972) 236:385-390.
Gantz, I. et al. Molecular Cloning of a Gene Encoding the Histamine H2 Receptor. Proc. Natl. Acad. Sci. USA (1991) 88:429-433.
Hill, S.J. et al. International Union of Pharmacology. XIII. Classification of Histamine Receptors. Pharmacol. Rev. (1997) 49(3):253-278.
Liu, C. et al. Cloning and Pharmacological Characterization of a Fourth Histamine Receptor (H4) Expressed in Bone Marrow. Mol. Pharmacol. (2001) 59(3):420-426.
Lovenberg, T.W. et al. Cloning and Functional Expression of the Human Histamine H3 Receptor. Mol. Pharmacol. (1999) 55(8):1101-1107.
Morse, K.L. et al. Cloning and Characterization of a Novel Human Histamine Receptor. J. Pharmacol. Exp. Ther. (2001) 296(3):1058-1066.
Nguyen, T. et al. Discovery of a Novel Member of the Histamine Receptor Family. Mol. Pharmacol. (2001) 59(3):427-433.
Oda, T. et al. Molecular Cloning and Characterization of a Novel Type of Histamine Receptor Preferentially Expressed in Leukocytes, J. Biol. Chem. (2000) 275(47):36781-36786.
Raible, D.G. et al. Pharmacologic Characterization of a Novel Histamine Receptor on Human Eosinophile. Am. J. Respir. Crit. Care Med. (1994) 149:1506-1511.
Yamashita, M. et al. Expression Cloning of a cDNA Encoding the Bovine Histamine H1 Receptor. Proc. Natl. Acad. Sci. USA (1991) 88:11515-11519.
Zhu, Y. et al. Cloning, Expression, and Pharmacological Characterization of a Novel Human Histamine Receptor. Mol. Pharmacol. (2001) 59(3):434-441.
PCT International Search Report, dated Mar. 2, 2004, for PCT Appln. No. PCT/US03/28017.

* cited by examiner

*Primary Examiner*—James O. Wilson
*Assistant Examiner*—Paul V. Ward

(57) ABSTRACT

Certain thienopyrrolyl and furanopyrrolyl compounds are disclosed as useful to treat or prevent disorders and conditions mediated by the histamine $H_4$ receptor, including allergic rhinitis.

2 Claims, No Drawings

HETEROCYCLIC COMPOUNDS

This application is a continuation of U.S. patent application Ser. No. 10/656,059, filed Sep. 5, 2003, now U.S. Pat. No. 7,226,938, which in turn claims the benefit of U.S. provisional patent application Ser. No. 60/408,723, filed Sep. 6, 2002.

FIELD OF THE INVENTION

The invention relates to novel, pharmaceutically active, fused heterocyclic compounds and methods of using them to treat or prevent disorders and conditions mediated by the histamine $H_4$ receptor.

BACKGROUND OF THE INVENTION

Histamine was first identified as a hormone (G. Barger and H. H. Dale, *J. Physiol.* (*London*) 1910, 41:19-59) and has since been demonstrated to play a major role in a variety of physiological processes, including the inflammatory "triple response" via $H_1$ receptors (A. S. F. Ash and H. O. Schild, *Br. J. Pharmac. Chemother.* 1966, 27:427-439), gastric acid secretion via $H_2$ receptors (J. W. Black et al., *Nature* 1972, 236:385-390), and neurotransmitter release in the central nervous system via $H_3$ receptors (J.-M. Arrang et al., *Nature* 1983, 302:832-837) (for review see S. J. Hill et al., *Pharmacol. Rev.* 1997, 49(3):253-278). All three histamine receptor subtypes have been demonstrated to be members of the superfamily of G protein-coupled receptors (I. Gantz et al., *Proc. Natl. Acad. Sci. U.S.A.* 1991, 88:429-433; T. W. Lovenberg et al., *Mol. Pharmacol.* 1999, 55(6):1101-1107; M. Yamashita et al., *Proc. Natl. Acad. Sci. U.S.A.* 1991, 88:11515-11519). There are, however, additional functions of histamine that have been reported, for which no receptor has been identified. For example, in 1994, Raible et al. demonstrated that histamine and R-α-methylhistamine could activate calcium mobilization in human eosinophils (D. G. Raible et al., *Am. J. Respir. Crit. Care Med.* 1994, 149:1506-1511). These responses were blocked by the $H_3$-receptor antagonist thioperamide. However, R-α-methylhistamine was significantly less potent than histamine, which was not consistent with the involvement of known $H_3$ receptor subtypes. Therefore, Raible et al. hypothesized the existence of a novel histamine receptor on eosinophils that was non-$H_1$, non-$H_2$, and non-$H_3$. Most recently several groups (T. Oda et al., *J. Biol. Chem.* 2000, 275(47):36781-36786; C. Liu et al., *Mol. Pharmacol.* 2001, 59(3):420-426; T. Nguyen et al., *Mol. Pharmacol.* 2001, 59(3):427-433; Y. Zhu et al., *Mol. Pharmacol.* 2001, 59(3):434-441; K. L. Morse et al., *J. Pharmacol. Exp. Ther.* 2001, 296(3):1058-1066) have identified and characterized a fourth histamine receptor subtype, the $H_4$ receptor. This receptor is a 390 amino acid, seven-transmembrane, G protein-coupled receptor with approximately 40% homology to the histamine $H_3$ receptor. In contrast to the $H_3$ receptor, which is primarily located in the brain, the $H_4$ receptor is expressed at greater levels in neutrophils and mast cells, among other cells, as reported by Morse et al. (see above).

Events that elicit the inflammatory response include physical stimulation (including trauma), chemical stimulation, infection, and invasion by a foreign body. The inflammatory response is characterized by pain, increased temperature, redness, swelling, reduced function, or a combination of these. Many conditions, such as allergies, asthma, chronic obstructed pulmonary disease (COPD), atherosclerosis, and autoimmune diseases, including rheumatoid arthritis and lupus, are characterized by excessive or prolonged inflammation. Inhibition of leukocyte recruitment can provide significant therapeutic value. Inflammatory diseases or inflammation-mediated diseases or conditions include, but are not limited to, acute inflammation, allergic inflammation, and chronic inflammation.

Mast cell de-granulation (exocytosis) leads to an inflammatory response that may be initially characterized by a histamine-modulated wheal and flare reaction. A wide variety of immunological (e.g., allergens or antibodies) and non-immunological (e.g., chemical) stimuli may cause the activation, recruitment, and de-granulation of mast cells. Mast cell activation initiates allergic ($H_1$) inflammatory responses, which in turn cause the recruitment of other effector cells that further contribute to the inflammatory response. The histamine H2 receptors modulate gastric acid secretion, and the histamine H3 receptors affect neurotransmitter release in the central nervous system.

Examples of textbooks on the subject of inflammation include J. I. Gallin and R. Snyderman, *Inflammation: Basic Principles and Clinical Correlates*, $3^{rd}$ Edition, (Lippincott Williams & Wilkins, Philadelphia, 1999); V. Stvrtinova, J. Jakubovsky and 1. Hulin, "Inflammation and Fever", *Pathophysiology Principles of Diseases* (Textbook for Medical Students, Academic Press, 1995); Cecil et al., *Textbook Of Medicine*, $18^{th}$ Edition (W.B. Saunders Company, 1988); and Steadmans Medical Dictionary.

SUMMARY OF THE INVENTION

The invention features a compound of formula (I):

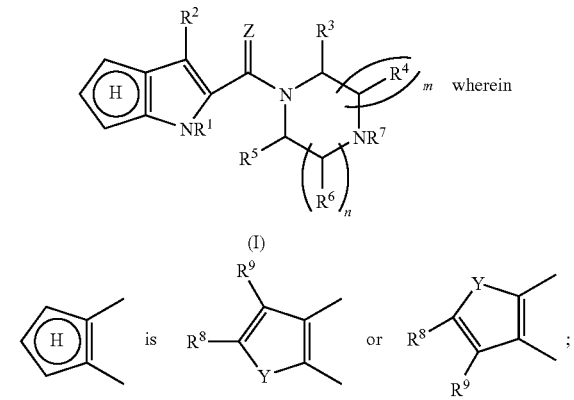

Y is O or S;
Z is O or S;
n is 1 or 2;
m is 1 or 2;
n+m is 2 or 3;
$R^1$ is H or $C_{1-6}$alkyl;
$R^2$ is H, F, Cl, Br or $C_{1-6}$alkyl;
$R^3$ and $R^4$ are, independently, H, $C_{1-4}$alkyl, $C_{3-6}$cycloalkyl, $C_{1-4}$alkyl($C_{3-6}$cycloalkyl), cyano, —$CF_3$, —(CO)$NR^pR^q$, —(CO)$OR^r$, —$CH_2NR^pR^q$ or —$CH_2OR^r$; where $R^p$, $R^q$ and $R^r$ are independently selected from H, $C_{1-4}$alkyl, $C_{3-6}$cycloalkyl, phenyl, —$C_{1-2}$alkyl($C_{3-6}$cycloalkyl), benzyl or phenethyl, or $R^p$ and $R^q$ taken together with the nitrogen to which they are attached, form a 4-7 membered heterocyclic ring with 0 or 1 additional heteroatoms selected from O, S, NH or $NC_{1-6}$alkyl, and where any phenyl or alkyl or cycloalkyl moiety of the foregoing is optionally and independently substituted with between 1 and 3 substituents selected from $C_{1-3}$alkyl, halo, hydroxy, amino, and $C_{1-3}$alkoxy;

$R^5$ and $R^6$ are, independently, H or $C_{1-4}$alkyl;

$R^7$ is —$R^a$, —$R^b R^a$, —$R^e$—O—$R^a$ or —$R^e$—N($R^c$)($R^d$), where $R^a$ is H, cyano, —(C=O)N($R^c$)($R^d$), —C(=NH)(NH$_2$), $C_{1-10}$alkyl, $C_{2-8}$alkenyl, $C_{3-8}$cycloalkyl, $C_{4-7}$heterocyclic radical or phenyl, where the $C_{4-7}$heterocyclic radical is attached at a carbon atom and contains one of O, S, NH or N$C_{1-4}$alkyl, and optionally an additional NH or N$C_{1-6}$alkyl in rings of 5 or 6 or 7 members, where Rb is $C_{1-8}$alkylene or $C_{2-8}$alkenylene, where $R^e$ is $C_{2-8}$alkylene or $C_{2-8}$alkenylene, where $R^c$ and $R^d$ are each independently H, $C_{1-4}$alkyl, $C_{2-4}$alkenyl, $C_{3-6}$cycloalkyl or phenyl, or $R^c$ and $R^d$ taken together with the nitrogen to which they are attached, form a 4-7 membered heterocyclic ring with 0 or 1 additional heteroatoms selected from O, S, NH or N$C_{1-6}$ alkyl, and where any phenyl or alkyl or cycloalkyl moiety of the foregoing is optionally and independently substituted with between 1 and 3 substituents selected from $C_{1-3}$alkyl, halo, hydroxy, amino, and $C_{1-3}$alkoxy; alternatively, $R^7$ may be taken together with an adjacent $R^4$ as well as their carbon and nitrogen of attachment to form a 5, 6 or 7 membered heterocyclic ring, with 0 or 1 additional heteroatoms selected from O, S, NH or N$C_{1-6}$alkyl, and optionally and independently substituted with between 1 and 3 substituents selected from $C_{1-3}$alkyl, halo, hydroxy, amino, and $C_{1-3}$alkoxy;

$R^8$ and $R^9$ are, independently, H, F, Cl, Br, I, $C_{1-4}$alkyl, $C_{1-4}$alkoxy, —$C_{3-6}$cycloalkyl, —O$C_{3-6}$cycloalkyl, —OCH$_2$Ph, —CF$_3$, —OCF$_3$, —SCF$_3$, —(C=O)$R^k$ (wherein $R^k$ is H, $C_{1-4}$alkyl, —OH, phenyl, benzyl, phenethyl or $C_{1-6}$alkoxy), —(N—$R^t$)(C=O)$R^k$ (where $R^t$ is H or $C_{1-4}$alkyl), —(N—$R^t$)SO$_2$$C_{1-4}$alkyl, —(S=(O)$_p$)—$C_{1-4}$ alkyl (wherein p is 0, 1 or 2), nitro, —SO$_2$N$R^l R^m$ (wherein $R^l$ and $R^m$ are independently selected from H, $C_{1-4}$alkyl, phenyl, benzyl or phenethyl, or $R^l$ and $R^m$ taken together with the nitrogen to which they are attached, form a 4-7 membered heterocyclic ring with 0 or 1 additional heteroatoms selected from O, S, NH or N$C_{1-4}$alkyl), —(C=O)N$R^l R^m$, cyano or phenyl, where any phenyl or alkyl or cycloalkyl moiety of the foregoing is optionally and independently substituted with between 1 and 3 substituents selected from $C_{1-3}$alkyl, halo, hydroxy, amino, and $C_{1-3}$alkoxy;

and enantiomers, diastereomers and pharmaceutically acceptable salts and esters thereof, with the following provisos, that $R^6$ adjacent to N must be H where $R^4$ adjacent to N is other than H, that $R^7$ is not —CH$_2$CH$_2$OH; and that where the core molecule is a 4H-furo, then one of $R^4$ and $R^6$ adjacent to N must not be methyl when the other is hydrogen unless $R^6$ and $R^4$ are taken together to form a bridging moiety.

The invention also features pharmaceutical compositions containing such compounds and methods of using such compositions in the treatment or prevention of H$_4$-mediated diseases and conditions, particularly those wherein it is desirable to antagonize the H$_4$ receptor.

DETAILED DESCRIPTION

Preferably, Y is S.
Preferably, Z is O.
Preferably, n is 1 and m is 1.

Preferably, $R^1$ is selected from the group consisting of H or methyl.

Preferably, $R^2$ is H.

Preferably, $R^3$ and $R^4$ are, independently, selected from the group consisting of a) H, b) —CH$_3$, —CH$_2$CH$_3$, —CH$_2$CH$_2$CH$_3$, —CH(CH$_3$)$_2$, n-butyl, i-butyl, t-butyl, c) cyclopropyl, cyclopentyl, cyclohexyl, —CH$_2$cyclopropyl, —CH$_2$cyclopentyl, —CH$_2$cyclohexyl, —CH$_2$Ocyclopropyl, —CH$_2$Ocyclopentyl, —CH$_2$Ocyclohexyl, d) cyano, e) trifluoromethyl, f) —(C=O)NH$_2$, —(C=O)NH$C_{1-4}$alkyl, —(C=O)N($C_{1-4}$alkyl)$_2$, —(C=O)NHphenyl, —(C=O)pyrrolidin-1-yl, —(C=O)imidazolidin-1-yl, —(C=O)pyrazolidin-1-yl, —(C=O)piperidin-1-yl, —(C=O)piperazin-1-yl, —(C=O)morpholin-4-yl, —(C=O)thiomorpholin-4-yl, g) —COOH, —COOCH$_3$, —COOCH$_2$CH$_3$, —COOphenyl, —COObenzyl, h) —CH$_2$NH$_2$, —CH$_2$NH$C_{1-4}$alkyl, —CH$_2$N($C_{1-4}$alkyl)$_2$, —CH$_2$NHphenyl, —CH$_2$NHbenzyl, —CH$_2$pyrrolidin-1-yl, —CH$_2$imidazolidin-1-yl, —CH$_2$pyrazolidin-1-yl, —CH$_2$piperidin-1-yl, —CH$_2$piperazin-1-yl, —CH$_2$morpholin-4-yl, —CH$_2$thiomorpholin-4-yl, i) —CH$_2$OH, —CH$_2$CH$_2$OH, —CH$_2$CH$_2$CH$_2$OH, —CH$_2$OCH$_3$, —CH$_2$OCH$_2$CH$_3$, —CH$_2$OCH$_2$CH$_2$CH$_3$, —CH$_2$OCH(CH$_3$)$_2$, —CH$_2$O-n-butyl, —CH$_2$O-i-butyl, —CH$_2$O-t-butyl, —CH$_2$Ophenyl, —CH$_2$Obenzyl and —CH$_2$OCH$_2$cyclopropyl.

Most preferably, $R^3$ and $R^4$ are, independently, H or —CH$_3$.

Preferably, $R^5$ and $R^6$ are, independently, selected from the group consisting of H and methyl.

Most preferably, $R^5$ and $R^6$ are H.

Preferably, $R^7$ is selected from the group consisting of a) H, —CH$_2$CH$_2$CH$_2$OH, b) cyano, c) —(C=O)NH$_2$, —(C=O)NH$C_{1-4}$alkyl, —(C=O)N($C_{1-4}$alkyl)$_2$, —(C=O)NHphenyl, —(C=O)pyrrolidin-1-yl, —(C=O)imidazolidin-1-yl, —(C=O)pyrazolidin-1-yl, —(C=O)piperidin-1-yl, —(C=O)piperazin-1-yl, —(C=O)morpholin-4-yl, —(C=O)thiomorpholin-4-yl, —CH$_2$(C=O)NH$_2$, —CH$_2$(C=O)NH$C_{1-4}$alkyl, —CH$_2$(C=O)N($C_{1-4}$alkyl)$_2$, —CH$_2$(C=O)NHphenyl, —CH$_2$(C=O)pyrrolidin-1-yl, —CH$_2$(C=O)imidazolidin-1-yl, —CH$_2$(C=O)pyrazolidin-1-yl, —CH$_2$(C=O)piperidin-1-yl, —CH$_2$(C=O)piperazin-1-yl, —CH$_2$(C=O)morpholin-4-yl, —CH$_2$(C=O)thiomorpholin-4-yl, —CH$_2$CH$_2$O(C=O)NH$_2$, —CH$_2$CH$_2$O(C=O)NH$C_{1-4}$alkyl, —CH$_2$CH$_2$O(C=O)N($C_{1-4}$alkyl)$_2$, —CH$_2$CH$_2$O(C=O)NHphenyl, —CH$_2$CH$_2$O(C=O)pyrrolidin-1-yl, —CH$_2$CH$_2$O(C=O)imidazolidin-1-yl, —CH$_2$CH$_2$O(C=O)pyrazolidin-1-yl, —CH$_2$CH$_2$O(C=O)piperidin-1-yl, —CH$_2$CH$_2$O(C=O)piperazin-1-yl, —CH$_2$CH$_2$O(C=O)morpholin-4-yl, —CH$_2$CH$_2$O(C=O)thiomorpholin-4-yl, d) —C(=NH)(NH$_2$), —CH$_2$C(=NH)(NH$_2$), e) —CH$_3$, —CH$_2$CH$_3$, —CH$_2$CH$_2$CH$_3$, —CH(CH$_3$)$_2$, n-butyl, i-butyl, t-butyl, —CH$_2$CH$_2$OCH$_3$, —CH$_2$CH$_2$OCH$_2$CH$_3$, —CH$_2$CH$_2$OCH$_2$CH$_2$CH$_3$, —CH$_2$CH$_2$OCH(CH$_3$)$_2$, —CH$_2$CH$_2$O-n-butyl, —CH$_2$CH$_2$O-1-butyl, —CH$_2$CH$_2$O-t-butyl, f), —CH₂CH=CH₂, g) cyclopropyl, cyclopentyl, cyclohexyl, —CH₂cyclopropyl, —CH₂cyclopentyl, —CH₂cyclohexyl, —CH₂CH₂Ocyclopropyl, —CH₂CH₂Ocyclopentyl, —CH₂CH₂Ocyclohexyl, h) pyrrolidinyl, imidazolidinyl, pyrazolidinyl, piperidinyl, piperazinyl, morpholinyl, thiomorpholinyl, —CH₂pyrrolidinyl, —CH₂imidazolidinyl, —CH₂pyrazolidinyl, —CH₂piperidinyl, —CH₂piperazinyl, —CH₂morpholinyl, —CH₂thiomorpholinyl, i) —CH₂CH₂NH₂, —CH₂CH₂NHC$_{1-4}$alkyl, —CH₂CH₂N(C$_{1-4}$alkyl)₂, —CH₂CH₂NHphenyl, —CH₂CH₂pyrrolidin-1-yl, —CH₂CH₂₁midazolidin-1-yl, —CH₂CH₂pyrazolidin-1-yl, —CH₂CH₂piperidin-1-yl, —CH₂CH₂piperazin-1-yl, —CH₂CH₂morpholin-4-yl, —CH₂CH₂thiomorpholin-4-yl, j) phenyl, benzyl, phenethyl and benzyloxymethyl.

Most preferrably, R$^7$ is selected from the group consisting of H and —CH₃.

Preferred R$^7$ taken together with an adjacent R$^4$ as well as their carbon and nitrogen of attachment are pyrrolidin-1,2-yl, imidazolidin-1,2-yl, imidazolidin-1,5-yl, pyrazolidin-1,5-yl, piperidin-1,2-yl, piperazin-1,2-yl, morpholin-4,5-yl and thiomorpholin-4,5-yl.

Most preferred R$^7$ taken together with an adjacent R$^4$ as well as their carbon and nitrogen of attachment are pyrrolidin-1,2-yl and piperidin-1,2-yl.

Preferrably, R$^8$ and R$^9$ are, independently, selected from the group consisting of H, —F, —Cl, —Br, —I, —CH₃, —CH₂CH₃, —OCH₃, —OCH₂CH₃, —OCH(CH₃)₂, cyclopropyl, cyclobutyl, cyclopentyl, cyclohexyl, -Ocyclopentyl, -Ocyclohexyl, —CF₃, —OCF₃, —SCF₃, —COOH, —COOCH₃, —COOCH₂CH₃, —C(O)CH₃, —NHCOCH₃, —NCH₃COCH₃, —NHSO₂CH₃, —NCH₃SO₂CH₃, —SOCH₃, —SO₂CH₃, —NO₂, —SO₂NH₂, —SO₂NHCH₃, —SO₂N(CH₃)₂, —C(O)NH₂, —C(O)N(CH₃)₂, —C(O)NH(CH₃), —CN and phenyl.

Most preferrably, R$^8$ and R$^9$ are, independently, selected from the group consisting of hydrogen, methyl, chloro and bromo. Further, it is most preferred that one or both of R$^8$ and R$^9$ are not hydrogen.

The "pharmaceutically acceptable salts and esters thereof" refer to those salt and ester forms of the compounds of the present invention that would be apparent to the pharmaceutical chemist, i.e., those that are non-toxic and that would favorably affect the pharmacokinetic properties of said compounds of the present invention. Those compounds having favorable pharmacokinetic properties would be apparent to the pharmaceutical chemist, i.e., those that are non-toxic and that possess such pharmacokinetic properties to provide sufficient palatability, absorption, distribution, metabolism and excretion. Other factors, more practical in nature, that are also important in the selection are cost of raw materials, ease of crystallization, yield, stability, hygroscopicity, and flowability of the resulting bulk drug. In addition, acceptable salts of carboxylates include sodium, potassium, calcium and magnesium. Examples of suitable cationic salts include hydrobromic, hydroiodic, hydrochloric, perchloric, sulfuric, maleic, fumaric, malic, tartatic, citric, benzoic, mandelic, methanesulfonic, hydroethanesulfonic, benzenesulfonic, oxalic, pamoic, 2-naphthalenesulfonic, p-toluenesulfonic, cyclohexanesulfamic and saccharic. Examples of suitable esters include such esters where one or more carboxyl substituents is replaced with p-methoxybenzyloxycarbonyl, 2,4,6-trimethylbenzyloxycarbonyl, 9-anthryloxycarbonyl, CH₃SCH₂COO—, tetrahydrofur-2-yloxycarbonyl, tetrahydropyran-2-yloxycarbonyl, fur-2-uloxycarbonyl, benzoyl methoxycarbonyl, p-nitrobenzyloxycarbonyl, 4-pyridyl methoxycarbonyl, 2,2,2-trichloroethoxycarbonyl, 2,2,2-tribromoethoxycarbonyl, t-butyloxycarbonyl, t-amyloxycarbonyl, diphenylmethoxycarbonyl, triphenylmethoxycarbonyl, adamantyloxycarbonyl, 2-benzyloxyphenyloxycarbonyl, 4-methylthiophenyloxycarbonyl, or tetrahydropyran-2-yloxycarbonyl.

The provisos are based on a failure to find activity in at least one compound meeting the specifications of each proviso.

Preferred compounds of Formula I are compounds selected from the group consisting of:

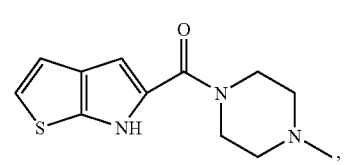
EX1

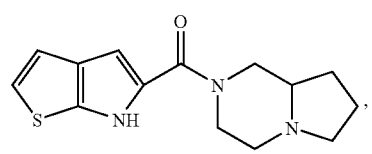
EX2

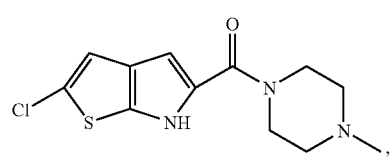
EX3

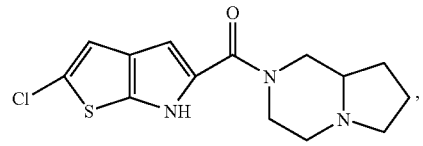
EX4

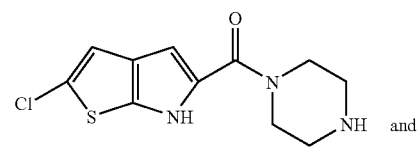
EX5 and

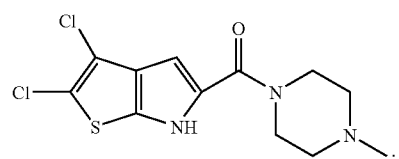
EX17

Additional preferred compounds of Formula I are compounds selected from the group consisting of:

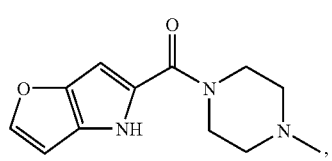
EX6

EX14
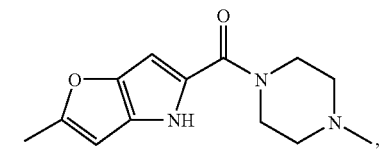
EX15
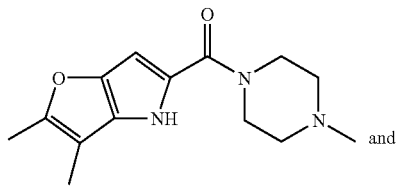 and
EX18
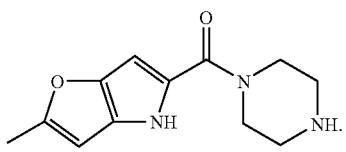
Additional preferred compounds of Formula I are compounds selected from the group consisting of:
EX7
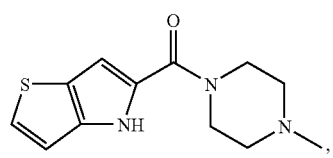
EX8
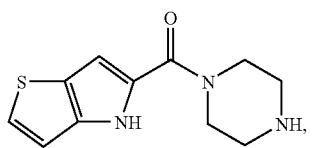
EX9
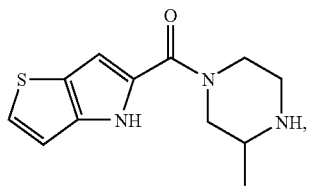
EX10
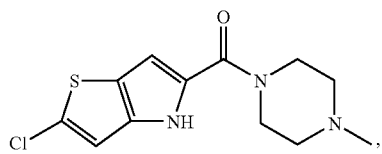
EX11
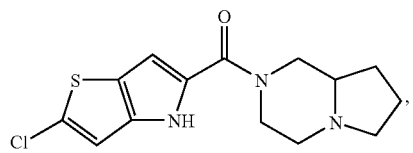
EX12
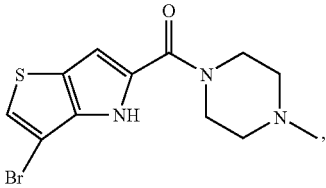
EX13
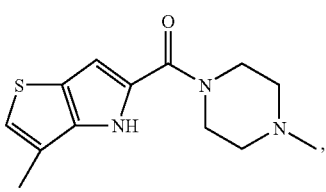
EX16
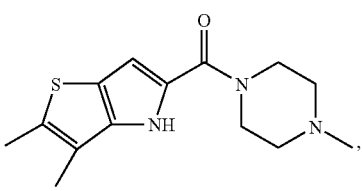
EX19
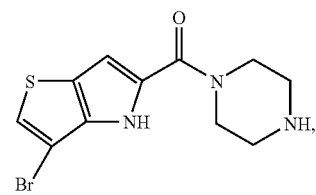
EX20
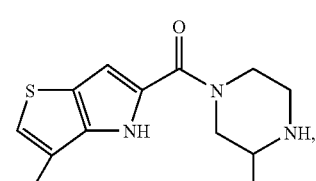
EX21
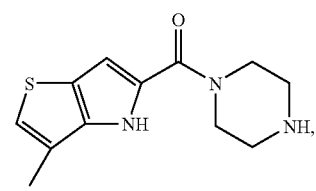
EX22
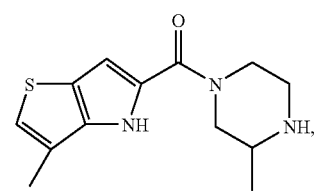
EX23

-continued

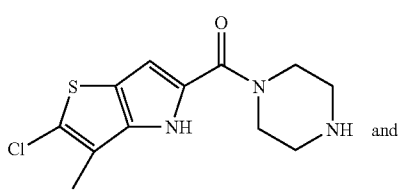
EX24

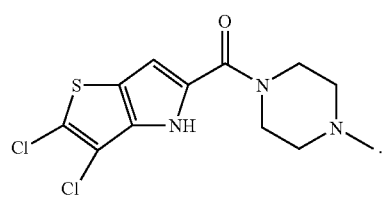
EX25

Still further preferred compounds are made according to the synthetic methods outlined in Schemes 1-4 where Y is S and selected from the group consisting of:

EX Compound
26  (2,3-Dimethyl-6H-thieno[2,3-b]pyrrol-5-yl)-(4-methyl-piperazin-1-yl)-methanone;
27 (2-Chloro-3-methyl-6H-thieno[2,3-b]pyrrol-5-yl)-(4-methyl-piperazin-1-yl)-methanone;
28 (3-Chloro-2-methyl-6H-thieno[2,3-b]pyrrol-5-yl)-(4-methyl-piperazin-1-yl)-methanone;
29 (2-Bromo-6H-thieno[2,3-b]pyrrol-5-yl)-(4-methyl-piperazin-1-yl)-methanone;
30 (3-Bromo-6H-thieno[2,3-b]pyrrol-5-yl)-(4-methyl-piperazin-1-yl)-methanone;
31  (4-Methyl-piperazin-1-yl)-(2-phenyl-6H-thieno[2,3-b]pyrrol-5-yl)-methanone;
32  [2-(4-Chloro-phenyl)-6H-thieno[2,3-b]pyrrol-5-yl]-(4-methyl-piperazin-1-yl)-methanone;
33  (3-Bromo-4H-thieno[3,2-b]pyrrol-5-yl)-(3,4-dimethyl-piperazin-1-yl)-methanone;
34 (3,4-Dimethyl-piperazin-1-yl)-(3-methyl-4H-thieno[3,2-b]pyrrol-5-yl)-methanone;
35 (2-Bromo-3-methyl-4H-thieno[3,2-b]pyrrol-5-yl)-(4-methyl-piperazin-1-yl)-methanone;
36 (3-Bromo-2-chloro-4H-thieno[3,2-b]pyrrol-5-yl)-(4-methyl-piperazin-1-yl)-methanone;
37  (2,3-Dichloro-4H-thieno[3,2-b]pyrrol-5-yl)-(3-methyl-piperazin-1-yl)-methanone;
38  (4-Methyl-piperazin-1-yl)-(2-phenyl-4H-thieno[3,2-b]pyrrol-5-yl)-methanone; and
39 (4-Methyl-piperazin-1-yl)-[2-(4-trifluoromethyl-phenyl)-4H-thieno[3,2-b]pyrrol-5-yl]-methanone.

The following terms are defined below, and by their usage throughout the disclosure.

"Alkyl" includes straight chain and branched hydrocarbons with at least one hydrogen removed to form a radical group. Alkyl groups include methyl, ethyl, propyl, isopropyl, butyl, isobutyl, t-butyl, 1-methylpropyl, pentyl, isopentyl, sec-pentyl, hexyl, heptyl, octyl, and so on. Alkyl does not include cycloalkyl.

"Alkenyl" includes straight chain and branched hydrocarbon radicals as above with at least one carbon-carbon double bond (sp$^2$). Alkenyls include ethenyl (or vinyl), prop-1-enyl, prop-2-enyl (or allyl), isopropenyl (or 1-methylvinyl), but-1-enyl, but-2-enyl, butadienyls, pentenyls, hexa-2,4-dienyl, and so on. Alkenyl does not include cycloalkyl.

"Alkoxy" includes a straight chain or branched alkyl group with a terminal oxygen linking the alkyl group to the rest of the molecule. Alkoxy includes methoxy, ethoxy, propoxy, isopropoxy, butoxy, t-butoxy, pentoxy and so on. "Aminoalkyl", "thioalkyl", and "sulfonylalkyl" are analogous to alkoxy, replacing the terminal oxygen atom of alkoxy with, respectively, NH (or NR), S, and SO$_2$.

"Cycloalkyl" includes cyclopropyl, cyclobutyl, cyclopentyl, cyclohexyl, cycloheptyl, cyclooctyl, and so on.

"Halo" includes fluoro, chloro, bromo, and iodo, and preferably fluoro or chloro.

"Patient" or "subject" includes mammals such as humans and animals (dogs, cats, horses, rats, rabbits, mice, non-human primates) in need of observation, experiment, treatment or prevention in connection with the relevant disease or condition. Preferably, the patient is a human.

"Composition" includes a product comprising the specified ingredients in the specified amounts as well as any product that results directly or indirectly from combinations of the specified ingredients in the specified amounts.

The compounds as described above may be made according to processes within the skill of the art and/or that are described in the schemes and examples that follow. To obtain the various compounds herein, starting materials may be employed that carry the ultimately desired substituents though the reaction scheme with or without protection as appropriate. Alternatively, it may be necessary to employ, in the place of the ultimately desired substituent, a suitable group that may be carried through the reaction scheme and replaced as appropriate with the desired substituent.

SCHEME 1

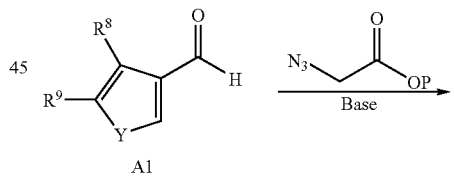

A1

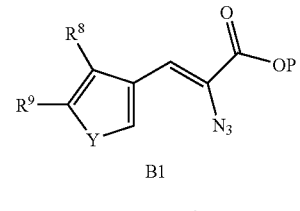

B1

Δ↓

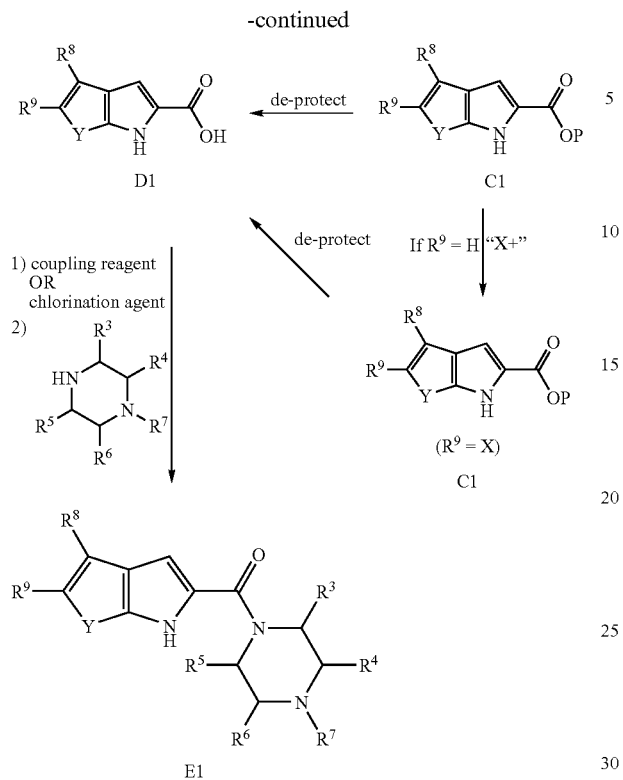

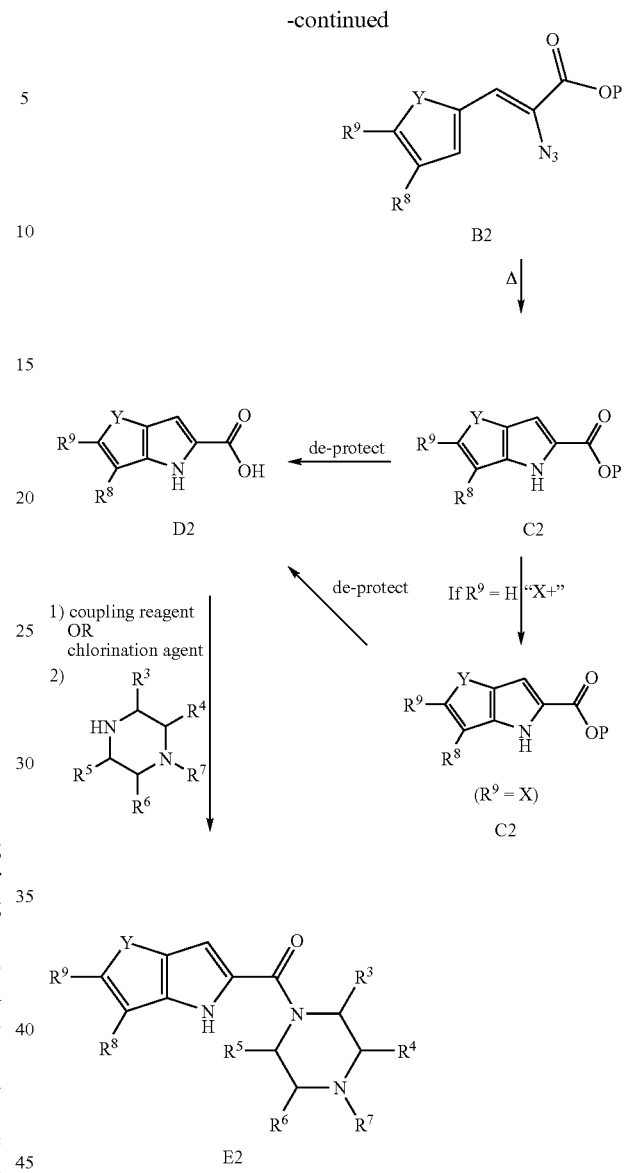

Referring to Scheme 1, there are disclosed the following notes and additions. Various $R^1$ may be obtained from E1 or C1 by treatment with a base and an appropriate alkylating agent. Where $R^2$ is halo, it may be obtained by treatment of E1 and C1 with an appropriate halogenating agent. Where $R^2$ is alkyl, it may be obtained by replacing the aldehyde of A1 with a ketone. P may be an alkyl, aryl or benzyl. Suitable bases include NaOEt, LDA, NaH, DBU, etc. The conversion of B1 to C1 is thermolytic with typical temperatures ranging from 80 to 200° C. Suitable solvents for the conversion of B1 to C1 are xylene, cumene, diphenylether, etc. Acidic or basic hydrolysis will provide deprotection. In the case where P is benzyl, hydrogenolysis is also useful for deprotection. Typical coupling reagents for the conversion of D1 to E1 include EDCI, HBTU, etc. Typical chlorination agents for the conversion of D1 to E1 include oxalyl chloride and thionyl chloride. X is a halogenating agent such as $Cl_2$, N-bromosuccinimide, TAS-F, $Br_2$, N-chlorosuccinimide, etc.

SCHEME 2

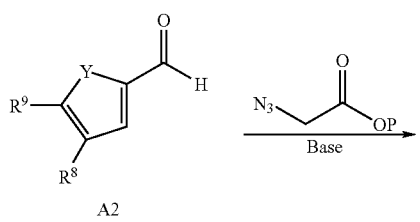

Referring to Scheme 2, there are disclosed the following notes and additions. Various $R^1$ may be obtained from E2 or C2 by treatment with a base and an appropriate alkylating agent. Where $R^2$ is halo, it may be obtained by treatment of E2 and C2 with an appropriate halogenating agent. Where $R^2$ is alkyl, it may be obtained by replacing the aldehyde of A2 with a ketone. P may be an alkyl, aryl or benzyl. Suitable bases include NaOEt, LDA, NaH, DBU, etc. The conversion of B2 to C2 is thermolytic with typical temperatures ranging from 80 to 200° C. Suitable solvents for the conversion of B2 to C2 are xylene, cumene, diphenylether, etc. Acidic or basic hydrolysis will provide deprotection. In the case where P is benzyl, hydrogenolysis is also useful for deprotection. Typical coupling reagents for the conversion of D2 to E2 include EDCI, HBTU, etc. Typical chlorination agents for the conversion of D2 to E2 include oxalyl chloride and thionyl chloride. X is a halogenating agent such as $Cl_2$, N-bromosuccinimide, TAS-F, $Br_2$, N-chlorosuccinimide, etc.

SCHEME 3

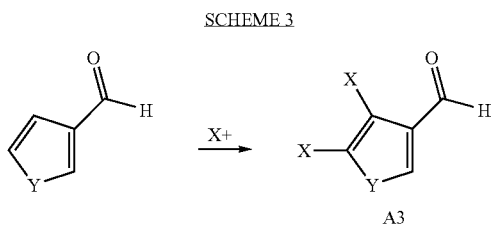

Referring to Scheme 3, there are disclosed the following notes and additions. X is a halogenating agent such as $Cl_2$, N-bromosuccinimide, TAS-F, $Br_2$, N-chlorosuccinimide, etc.

SCHEME 4

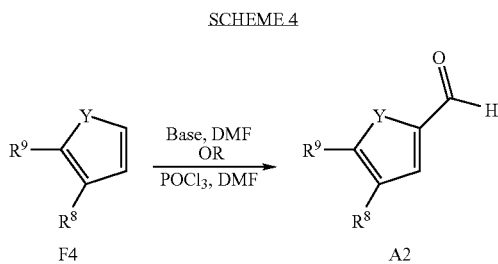

Referring to Scheme 4, there are disclosed the following notes and additions. Typical bases include n-BuLi, LDA, t-BuLi, KHMDS.

The expression of the $H_4$ receptor in immune cells, including some leukocytes and mast cells, establishes it as an important target for therapeutic intervention in a range of immunological and inflammatory disorders (such as allergic, chronic, or acute inflammation). Specifically $H_4$ receptor ligands are expected to be useful for the treatment or prevention of various mammalian disease states.

Thus, according to the invention, the disclosed compounds, where antagonists of the $H_4$ receptor, and compositions are useful for the amelioration of symptoms associated with, the treatment of, and the prevention of, the following conditions and diseases: inflammatory disorders, asthma, psoriasis, rheumatoid arthritis, ulcerative colitis, Crohn's disease, inflammatory bowel disease, multiple sclerosis, allergic disorders, allergic rhinitis, dermatological disorders, autoimmune disease, lymphatic disorders, atherosclerosis, and immunodeficiency disorders. The disclosed compounds may also be useful as adjuvants in chemotherapy or in the treatment of itchy skin.

Aspects of the invention include (a) a pharmaceutical composition comprising a compound of formula (I), or one or more preferred compounds as described herein, and a pharmaceutically acceptable carrier; (b) a packaged drug comprising (1) a pharmaceutical composition comprising a compound of formula (I) and a pharmaceutically acceptable carrier, and (2) instructions for the administration of said composition for the treatment or prevention of an $H_4$-mediated disease or condition.

The invention also provides a method for treating an $H_4$-mediated condition in a patient, said method comprising administering to the patient a pharmaceutically effective amount of a composition comprising a compound of formula (I) and other disclosed or preferred compounds. For example, the invention features a method for treating an $H_4$ mediated condition in a patient, said method comprising administering to the patient a pharmaceutically effective $H_4$-antagonizing amount of a composition comprising a compound of formula (I).

The effect of an antagonist may also be produced by an inverse agonist. Inverse agonism describes the property of a compound to actively turn off a receptor that displays constitutive activity. Constitutive activity can be identified in cells that have been forced to over-express the human $H_4$ receptor. Constitutive activity can be measured by examining cAMP levels or by measuring a reporter gene sensitive to cAMP levels after a treatment with a cAMP-stimulating agent such as forskolin. Cells that over-express $H_4$ receptors will display lower cAMP levels after forskolin treatment than non-expressing cells. Compounds that behave as $H_4$ agonists will dose-dependently lower forskolin-stimulated cAMP levels in $H_4$-expressing cells. Compounds that behave as inverse $H_4$ agonists will dose-dependently stimulate cAMP levels in $H_4$-expressing cells. Compounds that behave as $H_4$ antagonists will block either $H_4$ agonist-induced inhibition of cAMP or inverse $H_4$ agonist-induced increases in cAMP.

Further embodiments of the invention include disclosed compounds that are inhibitors of a mammalian histamine $H_4$ receptor function, inhibitors of inflammation or inflammatory responses in vivo or in vitro, modulators of the expression of a mammalian histamine $H_4$ receptor protein, inhibitors of polymorphonuclear leukocyte activation in vivo or in vitro, or combinations of the above, and corresponding methods of treatment, prophylaxis, and diagnosis comprising the use of a disclosed compound.

Those skilled in the art will be able to determine, according to known methods, the appropriate dosage for a patient, taking into account factors such as age, weight, general health, the type of symptoms requiring treatment, and the presence of other medications. In general, an effective amount will be between 0.01 and 1000 mg/kg per day, preferably between 0.5 and 300 mg/kg body weight, and daily dosages will be between 10 and 5000 mg for an adult subject of normal weight. Capsules, tablets or other formulations (such as liquids and film-coated tablets) may be of between 0.5 and 200 mg, such as 1, 3, 5, 10, 15, 25, 35, 50 mg, 60 mg, and 100 mg and can be administered according to the disclosed methods.

Dosage unit forms include tablets, capsules, pills, powders, granules, aqueous and nonaqueous oral solutions and suspensions, and parenteral solutions packaged in containers adapted for subdivision into individual doses. Dosage unit forms can also be adapted for various methods of administration, including controlled release formulations, such as subcutaneous implants. Administration methods include oral, rectal, parenteral (intravenous, intramuscular, subcutaneous), intracisternal, intravaginal, intraperitoneal, intravesical, local (drops, powders, ointments, gels or cream), and by inhalation (a buccal or nasal spray).

Parenteral formulations include pharmaceutically acceptable aqueous or nonaqueous solutions, dispersion, suspensions, emulsions, and sterile powders for the preparation thereof. Examples of carriers include water, ethanol, polyols (propylene glycol, polyethylene glycol), vegetable oils, and injectable organic esters such as ethyl oleate. Fluidity can be maintained by the use of a coating such as lecithin, a surfactant, or maintaining appropriate particle size. Carriers for solid dosage forms include (a) fillers or extenders, (b) binders, (c) humectants, (d) disintegrating agents, (e) solution retarders, (f) absorption accelerators, (g) adsorbants, (h) lubricants, (i) buffering agents, and (j) propellants.

Compositions may also contain adjuvants such as preserving, wetting, emulsifying, and dispensing agents; antimicrobial agents such as parabens, chlorobutanol, phenol, and sorbic acid; isotonic agents such as a sugar or sodium chloride; absorption-prolonging agents such as aluminum monostearate and gelatin; and absorption-enhancing agents.

EXAMPLES

General Synthetic Procedures

Procedure A: Annulation of Aldehyde with Ethyl Azidoacetate

A solution of aldehyde A1, A2 or A3 (1 equiv) and ethyl azidoacetate (4 equiv) was added dropwise to a solution of NaOEt (4 equiv) in EtOH (0.15 M) at 0° C. The reaction mixture was stirred at 0° C. for 1 h and at room temperature for an additional 1 h. The reaction mixture was then poured into satd aq $NH_4Cl$ and extracted with ether. The combined organics were dried ($Na_2SO_4$) and concentrated in vacuo. The residue was purified by silica gel column chromatography to provide the desired acrylate.

A solution of the resultant acrylate in xylene (0.2 M) was heated at 145° C. for 10-60 min and then allowed to cool to room temperature. The xylene solution was either cooled further to induce product crystallization or directly subjected to silica gel column chromatography to obtain the desired annulation product.

Procedure B: Ester Hydrolysis

A solution (0.2 M) of the ethyl ester (1 equiv, from Procedure A) and LiOH (5 equiv) in THF/MeOH/$H_2O$ (3:1:1) was heated at 65° C. overnight, cooled to room temperature, acidified with 2 N HCl, and extracted with EtOAc. The organic layer was separated, dried over $Na_2SO_4$, and concentrated to give the desired crude acid, which was taken to the next step without further purification.

Procedure C: Amide Formation Using 1-(3-Dimethylaminopropyl)-3-ethylcarbodimide Hydrochloride (EDCI)

A mixture of acid (1 equiv, from Procedure B), amine (1.5 equiv) and EDCI (2.0 equiv) in $CH_2Cl_2$ (0.2 M) was stirred at room temperature overnight and then partitioned between $CH_2Cl_2$ and satd aq $NaHCO_3$. The organic layer was separated, washed with $H_2O$, dried over $Na_2SO_4$, and concentrated. The crude product was further purified by silica gel column chromatography.

Procedure D: Amide Formation via Acyl Chloride Intermediate

A mixture of acid (1 equiv, from Procedure B) in $CH_2Cl_2$ (0.5 M) was treated at 0° C. with oxalyl chloride (1.2 equiv) followed by 1-2 drops of DMF. The reaction mixture was stirred at 0° C. for 30 min then slowly warmed to room temperature and stirred for an additional 1 h. All volatiles were removed to provide the crude acyl chloride.

The resultant acyl chloride was treated with amine (5.0 equiv) in $CH_2Cl_2$ (0.2 M) and allowed to stir at room temperature for 3 h. The reaction mixture was partitioned between $CH_2Cl_2$ and satd aq $NaHCO_3$. The organic layer was separated, washed with $H_2O$, dried over $Na_2SO_4$, and concentrated. The crude product was further purified with silica gel column chromatography.

General Analytical Procedures

NMR spectra were obtained on either a Bruker model DPX400 (400 MHz) or DPX500 (500 MHz) spectrometer. The format of the 1H NMR data below is: chemical shift in ppm down field of the tetramethylsilane reference (multiplicity, coupling constant J in Hz, integration).

Mass spectra were obtained on a Hewlett Packard (Agilent) series 1100 MSD using electrospray ionization (ESI) in either positive or negative mode as indicated. The "mass calculated" for a molecular formula is the monoisotopic mass of the compound.

Silica Gel Column Chromatography:

Normal-phase column chromatography was accomplished using an ISCO Foxy 200 system employing one of the following commercially available prepacked columns: ISCO Redisep ($SiO_2$, 10 g, 12 g, 35 g, 40 g, or 120 g).

Example 1

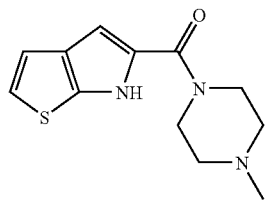

(4-Methyl-piperazin-1-yl)-(6H-thieno[2,3-b]pyrrol-5-yl)-methanone

A. 6H-Thieno[2,3-b]pyrrole-5-carboxylic acid ethyl ester. Thiophene-3-carbaldehyde (2.24 g, 20 mmol) was annulated according to Procedure A to provide the title compound (1.2 g, 31%) as a white solid. TLC (silica, 20% EtOAc/hexanes): $R_f$=0.50. $^1$H NMR ($CDCl_3$, 400 MHz): 10.30 (br s, 1H), 7.10 (d, J=1.9 Hz, 1H), 6.96 (d, J=5.4 Hz, 1H), 6.87 (d, J=5.4 Hz, 1H), 4.39 (q, J=7.1 Hz, 2H), 1.38 (t, J=7.1 Hz, 3H).

B. 6H-Thieno[2,3-b]pyrrole-5-carboxylic acid. 6H-Thieno[2,3-b]pyrrole-5-carboxylic acid ethyl ester (835 mg, 4.3 mmol) was hydrolyzed according to Procedure B to provide the crude acid as a pale-yellow solid. $^1$H NMR ($CD_3OD$, 400 MHz): 7.02 (s, 1H), 6.96 (s, 1H), 6.95 (s, 1H).

C. (4-Methyl-piperazin-1-yl)-(6H-thieno[2,3-b]pyrrol-5-yl)-methanone. 6H-Thieno[2,3-b]pyrrole-5-carboxylic acid (60 mg, 0.35 mmol) was coupled with N-methylpiperazine according to Procedure C to provide the title compound (44 mg, 50%) as a light yellow solid. TLC (silica, 10% MeOH/$CH_2Cl_2$): $R_f$=0.4. MS (electrospray): exact mass calculated for $C_{12}H_{15}N_3OS$, 249.09; m/z found, 250.1 [M+H]$^+$. $^1$H NMR ($CD_3OD$, 400 MHz, TFA salt): 6.97 (s, 1H), 6.96 (s, 1H), 6.85 (s, 1H), 4.20-3.10 (m, 8H), 2.96 (s, 3H).

Example 2

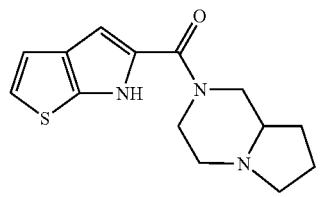

(Hexahydro-pyrrolo[1,2-a]pyrazin-2-yl)-(6H-thieno[2,3-b]pyrrol-5-yl)-methanone 6H-Thieno[2,3-b]pyrrole-5-carboxylic acid (60 mg, 0.35 mmol) was coupled with octahydro-pyrrolo[1,2-a]pyrazine according to Procedure C to provide the title compound (34 mg, 35%) as a light yellow solid. TLC (silica, 10% MeOH/CH$_2$Cl$_2$): R$_f$=0.4. MS (electrospray): exact mass calculated for C$_{14}$H$_{17}$N$_3$OS, 275.11; m/z found, 276.2 [M+H]$^+$. $^1$H NMR (CDCl$_3$, 400 MHz): 11.1 (br s, 1H), 6.96 (d, J=5.4 Hz, 1H), 6.87 (d, J=5.4 Hz, 1H), 6.71 (d, J=1.9 Hz, 1H), 4.84 (d, J=12.2 Hz, 1H), 4.70 (d, J=12.2 Hz, 1H), 3.30-2.90 (m, 4H), 2.30-1.40 (m, 7H).

Example 3

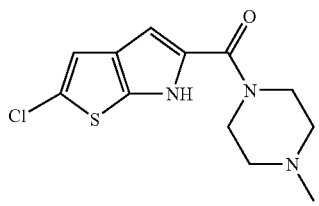

(2-Chloro-6H-thieno[2,3-b]pyrrol-5-yl)-(4-methyl-piperazin-1-yl)-methanone

A. 2-Chloro-6H-thieno[2,3-b]pyrrole-5-carboxylic acid ethyl ester. A solution of 6H-thieno[2,3-b]pyrrole-5-carboxylic acid ethyl ester (580 mg, 3.0 mmol) in acetic acid (6 mL) and CHCl$_3$ (6 mL) was treated with three portions of N-chlorosuccinimide (total 415 mg, 3.15 mmol) at 0° C. over 2 h. The reaction mixture was slowly warmed to room temperature and stirred overnight. The CHCl$_3$ was then removed, and the residue was basified with 4 N NaOH and extracted with EtOAc. The combined organics were washed with satd aq NaHCO$_3$, dried over Na$_2$SO$_4$, and concentrated. Column chromatography (SiO$_2$, 5-10% EtOAc/hexanes) gave 600 mg (88%) of a white solid. TLC (silica, 20% EtOAc/hexanes): R$_f$=0.5. $^1$H NMR (CDCl$_3$, 400 MHz): 10.5 (br s, 1H), 6.97 (d, J=2.0 Hz, 1H), 6.85 (s, 1H), 4.39 (q, J=7.2 Hz, 2H), 1.35 (t, J=7.2 Hz, 3H).

B. (2-Chloro-6H-thieno[2,3-b]pyrrol-5-yl)-(4-methyl-piperazin-1-yl)-methanone. 2-Chloro-6H-thieno[2,3-b]pyrrole-5-carboxylic acid ethyl ester (102 mg, 0.45 mmol) was hydrolyzed (Procedure B) and coupled with N-methylpiperazine (procedure D) to provide the title compound (102 mg, 80% for two steps) as an off-white solid. TLC (silica, 10% MeOH/CH$_2$Cl$_2$): R$_f$=0.4. MS (electrospray): exact mass calculated for C$_{12}$H$_{14}$ClN$_3$OS, 283.05; m/z found, 284.1 [M+H]$^+$. $^1$H NMR (CDCl$_3$, 400 MHz): 10.5 (br s, 1H), 6.87 (s, 1H), 6.61 (d, J=1.8 Hz, 1H), 3.92 (t, J=5.1 Hz, 4H), 2.50 (t, J=5.1 Hz, 4H), 2.35 (s, 3H).

Example 4

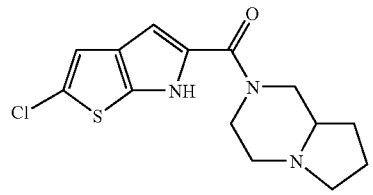

(2-Chloro-6H-thieno[2,3-b]pyrrol-5-yl)-(hexahydro-pyrrolo[1,2-a]pyrazin-2-yl)-methanone 2-Chloro-6H-thieno[2,3-b]pyrrole-5-carboxylic acid ethyl ester (102 mg, 0.45 mmol) was hydrolyzed (Procedure B) and then coupled with octahydro-pyrrolo[1,2-a]pyrazine (Procedure D) to provide the title compound (108 mg, 78% for two steps) as an off-white solid. TLC (silica, 10% MeOH/CH$_2$Cl$_2$): R$_f$=0.35. MS (electrospray): exact mass calculated for C$_{14}$H$_{16}$ClN$_3$OS, 309.07; m/z found, 310.1 [M+H]$^+$. $^1$H NMR (CDCl$_3$, 400 MHz): 11.1 (br s, 1H), 6.86 (s, 1H), 6.62 (s, 1H), 4.79 (d, J=11.8 Hz, 1H), 4.67 (d, J=11.8 Hz, 1H), 3.30-2.90 (m, 4H), 2.30-1.40 (m, 7H).

Example 5

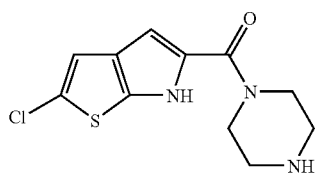

(2-Chloro-6H-thieno[2,3-b]pyrrol-5-yl)-piperazin-1-yl-methanone

2-Chloro-6H-thieno[2,3-b]pyrrole-5-carboxylic acid ethyl ester (102 mg, 0.45 mmol) was hydrolyzed (Procedure B) and then coupled with piperazine (Procedure D) to provide the title compound (42 mg, 35% for two steps) as an off-white solid. TLC (silica, 10% MeOH/CH$_2$Cl$_2$): R$_f$=0.15. MS (electrospray): exact mass calculated for C$_{11}$H$_{12}$ClN$_3$OS, 269.04;

m/z found, 270.1 [M+H]+. 1H NMR (CDCl3, 400 MHz): 10.5 (br s, 1H), 6.87 (s, 1H), 6.61 (s, 1H), 3.87 (t, J=4.8 Hz, 4H), 2.96 (t, J=5.2 Hz, 4H).

Example 6

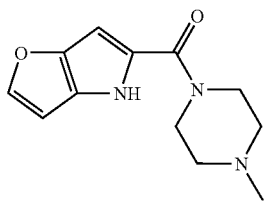

(4H-Furo[3,2-b]pyrrol-5-yl)-(4-methyl-piperazin-1-yl)-methanone

A. 4H-Furo[3,2-b]pyrrole-5-carboxylic acid ethyl ester. Furan-2-carbaldehyde (1.92 g, 20 mmol) was annulated according to procedure A to provide the title compound (1.97 g, 55%) as a white solid. TLC (silica, 20% EtOAc/hexanes): $R_f$=0.50. 1H NMR (CDCl3, 400 MHz): 8.95 (br s, 1H), 7.51 (d, J=2.2 Hz, 1H), 6.81-6.80 (m, 1H), 6.46-6.45 (m, 1H), 4.35 (q, J=7.1 Hz, 2H), 1.38 (t, J=7.1 Hz, 3H).

B. (4H-Furo[3,2-b]pyrrol-5-yl)-(4-methyl-piperazin-1-yl)-methanone. 4H-Furo[3,2-b]pyrrole-5-carboxylic acid ethyl ester (200 mg, 1.12 mmol) was hydrolyzed (Procedure B) and coupled with N-methylpiperazine (Procedure D) to provide the title compound (185 mg, 71% for two steps) as an off-white solid. TLC (silica, 10% MeOH/CH2Cl2): $R_f$=0.4. MS (electrospray): exact mass calculated for $C_{12}H_{15}N_3O_2$, 233.12; m/z found, 234.2 [M+H]+. 1H NMR (CDCl3, 400 MHz): 10.3 (br s, 1H), 7.43 (d, J=2.2 Hz, 1H), 6.43-6.42 (m, 2H), 3.90 (t, J=5.0 Hz, 4H), 2.47 (t, J=5.1 Hz, 4H), 2.32 (s, 3H).

Example 7

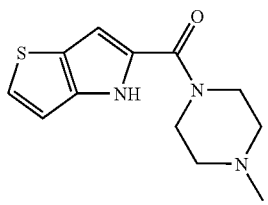

(4-Methyl-piperazin-1-yl)-(4H-thieno[3,2-b]pyrrol-5-yl)-methanone

A. 4H-Thieno[3,2-b]pyrrole-5-carboxylic acid ethyl ester. To a solution of thiophene-2-carbaldehyde (1.10 mL, 11.7 mmol) and ethyl azidoacetate (1.4 mL, 11.7 mmol) in EtOH (35 mL) cooled to 0° C. was added NaOEt (1.0 g, 14.7 mmol) in one portion. The mixture was allowed to reach room temperature over 14 h and was then poured into water (400 mL) and extracted with CH2Cl2 (3×50 mL). The combined organics were washed with water and brine, dried over Na2SO4, and concentrated. The residue was taken up in xylenes (10 mL), and the resulting solution was refluxed for 1 h. The solution was cooled and then loaded directly onto silica gel and purified (35 g SiO2, 10-20% EtOAc/hexanes) to reveal 0.12 g (5%) of a yellowish solid. 1H NMR (400 MHz, CDCl3): 9.06 (br s, 1H), 7.33 (d, J=5.3 Hz, 1H), 7.15-7.14 (m, 1H), 6.96 (dd, J=5.3, 0.8 Hz, 1H), 4.37 (q, J=7.3 Hz, 2H), 1.39 (t, J=7.3 Hz, 3H). 13C NMR (100 MHz, CDCl3): 161.3, 140.9, 129.2, 126.9, 124.6, 110.9, 107.3, 60.4, 14.2.

B. (4-Methyl-piperazin-1-yl)-(4H-thieno[3,2-b]pyrrol-5-yl)-methanone. To a solution of 4H-thieno[3,2-b]pyrrole-5-carboxylic acid ethyl ester (98.5 mg, 0.50 mmol) in wet THF (3 mL) was added LiOH (129 mg, 3 mmol). This mixture was stirred at room temperature for 3 days. The reaction mixture was diluted with water (50 mL), and 1 M HCL was added to adjust the pH to about 3. This mixture was then extracted with EtOAc, and the combined organics were dried over Na2SO4. The solvent was removed to reveal 73.4 mg (87%) of the free acid, which was used in the coupling event without further purification. The acid (73.4 mg, 0.44 mmol) was taken up in THF (3 mL), and CDI (87.1 mg, 0.54 mmol) was added in one portion. The reaction mixture was stirred for 1 h. To this mixture was then added 1-methylpiperazine (70 µL), and the mixture stirred for an additional 6 h. The reaction mixture was diluted with EtOAc, washed with water, NaHCO3 (aq) and then brine, and subsequently purified by column chromatography (10 g SiO2, 1-8% MeOH (2 M NH3)/CH2Cl2) to reveal 55.6 mg (51%) of the title compound. 1H NMR (400 MHz, CDCl3): 9.26 (br s, 1H), 7.26 (d, J=5.3 Hz, 1H), 6.97 (dd, J=5.3, 0.8 Hz, 1H), 6.75-6.74 (m, 1H), 4.07-3.88 (m, 4H), 2.68-2.48 (m, 4H), 2.43 (br s, 3H). MS (electrospray): exact mass calculated for $C_{12}H_{15}N_3OS$, 249.09; m/z found, 250.1 [M+H]+.

Example 8

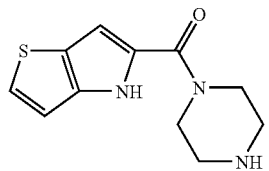

Piperazin-1-yl-(4H-thieno[3,2-b]pyrrol-5-yl)-methanone

4H-Thieno[3,2-b]pyrrole-5-carboxylic acid (50 mg, 0.30 mmol) was coupled with piperazine according to Procedure D to provide the title compound (25 mg, 35%) as an off-white solid. TLC (silica, 10% MeOH/CH2Cl2): $R_f$=0.15. MS (electrospray): exact mass calculated for $C_{11}H_{13}N_3OS$, 235.08; m/z found, 236.1 [M+H]+. 1H NMR (CD3OD, 400 MHz):

7.33 (d, J=5.3 Hz, 1H), 6.98 (dd, J=5.2, 0.7 Hz, 1H), 6.89 (d, J=0.6 Hz, 1H), 4.08 (t, J=5.3 Hz, 4H), 3.50-3.20 (m, 4H).

Example 9

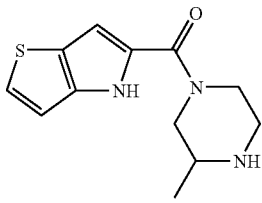

(3-Methyl-piperazin-1-yl)-(4H-thieno[3,2-b]pyrrol-5-yl)-methanone

4H-Thieno[3,2-b]pyrrole-5-carboxylic acid (50 mg, 0.30 mmol) was coupled with 2-methylpiperazine according to Procedure D to provide the title compound (58 mg, 78%) as an off-white solid. TLC (silica, 10% MeOH/CH$_2$Cl$_2$): R$_f$=0.15. MS (electrospray): exact mass calculated for C$_{12}$H$_{15}$N$_3$OS, 249.09; m/z found, 250.1 [M+H]$^+$. $^1$H NMR (CD$_3$OD, 400 MHz): 7.33 (d, J=5.3 Hz, 1H), 6.98 (d, J=5.3 Hz, 1H), 6.88 (s, 1H), 4.62-4.56 (m, 2H), 3.50-3.20 (m, 5H), 1.36 (d, J=6.6 Hz, 3H).

Example 10

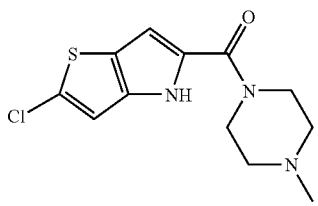

(2-Chloro-4H-thieno[3,2-b]pyrrol-5-yl)-(4-methyl-piperazin-1-yl)-methanone

A. 2-Chloro-4H-thieno[3,2-b]pyrrole-5-carboxylic acid ethyl ester. 5-Chloro-thiophene-2-carbaldehyde (2.92 g, 20 mmol) was annulated according to Procedure A to provide the title compound (2.8 g, 61%) as a white solid. TLC (silica, 20% EtOAc/hexanes): R$_f$=0.48. $^1$H NMR (CDCl$_3$, 400 MHz): 9.10 (br s, 1H), 7.04 (dd, J=1.9, 0.7 Hz, 1H), 6.89 (d, J=0.7 Hz, 1H), 4.37 (q, J=7.2 Hz, 2H), 1.39 (t, J=7.2 Hz, 3H).

B. (2-Chloro-4H-thieno[3,2-b]pyrrol-5-yl)-(4-methyl-piperazin-1-yl)-methanone. 2-Chloro-4H-thieno[3,2-b]pyrrole-5-carboxylic acid ethyl ester (230 mg, 1.0 mmol) was hydrolyzed (Procedure B) and then coupled with N-methylpiperazine (Procedure C) to provide the title compound (128 mg, 45% for two steps) as an off-white solid. TLC (silica, 10% MeOH/CH$_2$Cl$_2$): R$_f$=0.4. MS (electrospray): exact mass calculated for C$_{12}$H$_{14}$ClN$_3$OS, 283.05; m/z found, 284.1 [M+H]$^+$. $^1$H NMR (CDCl$_3$, 400 MHz): 10.1 (br s, 1H), 6.88 (s, 1H), 6.64 (d, J=1.4 Hz, 1H), 3.91 (t, J=4.4 Hz, 4H), 2.49 (t, J=5.1 Hz, 4H), 2.35 (s, 3H).

Example 11

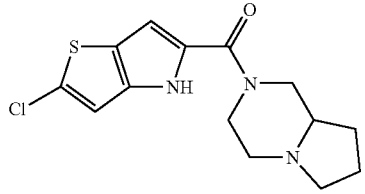

(2-Chloro-4H-thieno[3,2-b]pyrrol-5-yl)-(hexahydro-pyrrolo[1,2-a]pyrazin-2-yl)-methanone 2-Chloro-4H-thieno[3,2-b]pyrrole-5-carboxylic acid ethyl ester (230 mg, 1.0 mmol) was hydrolyzed (Procedure B) and then coupled with octahydro-pyrrolo[1,2-a]pyrazine (Procedure C) to provide the title compound (93 mg, 30% for two steps) as an off-white solid. TLC (silica, 10% MeOH/CH$_2$Cl$_2$): R$_f$=0.4. MS (electrospray): exact mass calculated for C$_{14}$H$_{16}$ClN$_3$OS, 309.07; m/z found, 310.1 [M+H]$^+$. $^1$H NMR (CDCl$_3$, 400 MHz): 10.9 (br s, 1H), 6.86 (s, 1H), 6.64 (d, J=1.4 Hz, 1H), 4.77 (d, J=12.2 Hz, 1H), 4.65 (d, J=12.7 Hz, 1H), 3.30-2.90 (m, 4H), 2.30-1.40 (m, 7H).

Example 12

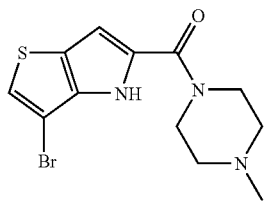

(3-Bromo-4H-thieno[3,2-b]pyrrol-5-yl)-(4-methyl-piperazin-1-yl)-methanone

A. 3-Bromo-4H-thieno[3,2-b]pyrrole-5-carboxylic acid ethyl ester. 4-Bromo-thiophene-2-carbaldehyde (3.8 g, 20 mmol) was annulated according to Procedure A to provide the title compound (1.2 g, 22%) as a white solid. TLC (silica, 20% EtOAc/hexanes): R$_f$=0.48. $^1$H NMR (CDCl$_3$, 400 MHz): 9.58 (br s, 1H), 7.20 (s, 1H), 7.15 (d, J=1.5 Hz, 1H), 4.41 (q, J=7.2 Hz, 2H), 1.39 (t, J=7.2 Hz, 3H).

B. (3-Bromo-4H-thieno[3,2-b]pyrrol-5-yl)-(4-methyl-piperazin-1-yl)-methanone. 3-Bromo-4H-thieno[3,2-b]pyrrole-5-carboxylic acid ethyl ester (67 mg, 0.24 mmol) was hydrolyzed (Procedure B) and then coupled with N-methylpiperazine (Procedure D) to provide the title compound (65 mg, 82% for two steps) as an off-white solid. TLC (silica, 10% MeOH/CH$_2$Cl$_2$): R$_f$=0.4. MS (electrospray): exact mass calculated for C$_{12}$H$_{14}$BrN$_3$OS, 327.00; m/z found, 328.0

[M+H]+. 1H NMR (CDCl3, 400 MHz): 9.95 (br s, 1H), 7.11 (s, 1H), 6.73 (d, J=1.8 Hz, 1H), 3.91 (t, J=5.1 Hz, 4H), 2.49 (t, J=5.1 Hz, 4H), 2.34 (s, 3H).

Example 13

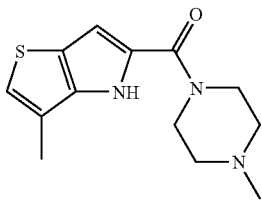

(4-Methyl-piperazin-1-yl)-(3-methyl-4H-thieno[3,2-b]pyrrol-5-yl)-methanone.

A. 4-methyl-thiophene-2-carbaldehyde. A solution of 3-methylthiophene (6.76 mL, 70 mmol) in ether (70 mL) was treated with n-butyllithium (2.5 M in hexanes, 28.6 mL, 71.4 mmol) at such a rate that a slight reflux was maintained. The reaction mixture was heated to reflux for 15 min and then DMF (7.0 mL, 91 mmol) in ether (30 mL) was added. After stirring for 4 h, the reaction was quenched with addition of satd aq NH4Cl (200 mL). The organic layer was separated, washed with brine and then H2O, dried over Na2SO4, and concentrated. Column chromatography (SiO2, 5-10% EtOAc/hexanes) provided a mixture of 4-methyl-thiophene-2-carbaldehyde and 3-methyl-thiophene-2-carbaldehyde (4.4:1, 8.1 g, 92%) as a light yellow oil. TLC (silica, 10% EtOAc/hexanes): $R_f$=0.55. For 4-methyl-thiophene-2-carbaldehyde: 1H NMR (CDCl3, 400 MHz): 9.95 (s, 1H), 7.58 (d, J=1.2 Hz, 1H), 7.37-7.35 (m, 1H), 2.32 (s, 3H). For 3-methyl-thiophene-2-carbaldehyde: 1H NMR (CDCl3, 400 MHz): 10.02 (s, 1H), 7.64 (d, J=4.6 Hz, 1H), 6.97 (d, J=4.6 Hz, 1H), 2.58 (s, 3H).

B. 3-Methyl-4H-thieno[3,2-b]pyrrole-5-carboxylic acid ethyl ester. The mixture of 4-methyl-thiophene-2-carbaldehyde and 3-methyl-thiophene-2-carbaldehyde (2.84 g, 22.5 mmol) was annulated according to Procedure A to provide the title compound (2.5 g, 65%) as a white solid. TLC (silica, 20% EtOAc/hexanes): $R_f$=0.45. 1H NMR (CDCl3, 400 MHz): 9.95 (br s, 1H), 7.12 (d, J=1.9 Hz, 1H), 6.90 (d, J=1.2 Hz, 1H), 4.39 (q, J=7.2 Hz, 2H), 2.35 (s, 3H), 1.39 (t, J=7.2 Hz, 3H).

C. (4-Methyl-piperazin-1-yl)-(3-methyl-4H-thieno[3,2-b]pyrrol-5-yl)-methanone. 3-Methyl-4H-thieno[3,2-b]pyrrole-5-carboxylic acid ethyl ester (200 mg, 0.96 mmol) was hydrolyzed (Procedure B) and then coupled with N-methylpiperazine (Procedure D) to provide the title compound (197 mg, 78% for two steps) as an off-white solid. TLC (silica, 10% MeOH/CH2Cl2): $R_f$=0.4. MS (electrospray): exact mass calculated for C13H17N3OS, 263.1 1; m/z found, 264.1 [M+H]+. 1H NMR (CDCl3, 400 MHz): 11.10 (br s, 1H), 6.76 (d, J=1.2 Hz, 1H), 6.69 (d, J=2.0 Hz, 1H), 3.94-3.90 (m, 4H), 2.47 (t, J=5.1 Hz, 4H), 2.33 (s, 3H), 2.25 (s, 3H).

Example 14

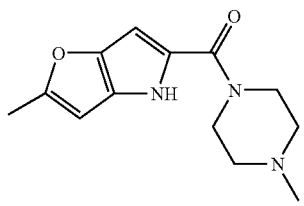

(2-Methyl-4H-furo[3,2-b]pyrrol-5-yl)-(4-methyl-piperazin-1-yl)-methanone

A. 2-Methyl-4H-furo[3,2-b]pyrrole-5-carboxylic acid ethyl ester. 5-Methyl-furan-2-carbaldehyde (2.2 g, 20 mmol) was annulated according to Procedure A to provide the title compound (2.89 g, 75%) as a white solid. TLC (silica, 10% EtOAc/hexanes): $R_f$=0.4. 1H NMR (CDCl3, 400 MHz): 9.50 (br s, 1H), 6.73 (s, 1H), 6.04 (s, 1H), 4.35 (q, J=7.2 Hz, 2H), 2.37 (s, 3H), 1.35 (t, J=7.2 Hz, 3H).

B. (2-Methyl-4H-furo[3,2-b]pyrrol-5-yl)-(4-methyl-piperazin-1-yl)-methanone. 2-Methyl-4H-furo[3,2-b]pyrrole-5-carboxylic acid ethyl ester (200 mg, 1.04 mmol) was hydrolyzed (Procedure B) and then coupled with N-methylpiperazine (Procedure D) to provide the title compound (208 mg, 81% for two steps) as a white solid. TLC (silica, 10% MeOH/CH2Cl2): $R_f$=0.35. MS (electrospray): exact mass calculated for C13H17N3O2, 247.13; m/z found, 248.2 [M+H]+. 1H NMR (CDCl3, 400 MHz): 9.85 (br s, 1H), 6.36 (s, 1H), 6.07 (s, 1H), 3.87 (t, J=5.0 Hz, 4H), 2.47 (t, J=5.2 Hz, 4H), 2.39 (s, 3H), 2.33 (s, 3H).

Example 15

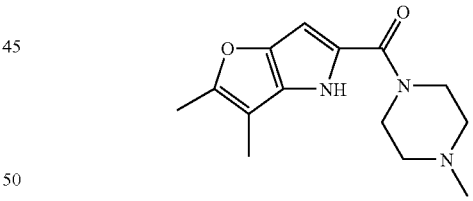

(2,3-Dimethyl-4H-furo[3,2-b]pyrrol-5-yl)-(4-methyl-piperazin-1-yl)-methanone

A. 2,3-Dimethyl-4H-furo[3,2-b]pyrrole-5-carboxylic acid ethyl ester. 4,5-Dimethyl-furan-2-carbaldehyde (2.2 g, 18 mmol) was annulated according to Procedure A to provide the title compound (1.76 g, 48%) as an off-white solid. TLC (silica, 10% EtOAc/hexanes): $R_f$=0.35. 1H NMR (CDCl3, 400 MHz): 8.95 (br s, 1H), 6.69 (d, J=1.7 Hz, 1H), 4.32 (q, J=7.2 Hz, 2H), 2.33 (s, 3H), 2.08 (s, 3H), 1.37 (t, J=7.2 Hz, 3H).

B. (2,3-Dimethyl-4H-furo[3,2-b]pyrrol-5-yl)-(4-methyl-piperazin-1-yl)-methanone. 2,3-Dimethyl-4H-furo[3,2-b]pyrrole-5-carboxylic acid ethyl ester (200 mg, 0.97 mmol)

was hydrolyzed (Procedure B) and then coupled with N-methylpiperazine (Procedure D) to provide the title compound (190 mg, 75% for two steps) as an off-white solid. TLC (silica, 10% MeOH/CH$_2$Cl$_2$): R$_f$=0.35. MS (electrospray): exact mass calculated for C$_{14}$H$_{19}$N$_3$O$_2$, 261.15; m/z found, 261.8 [M+H]$^+$. $^1$H NMR (CDCl$_3$, 400 MHz): 9.95 (br s, 1H), 6.32 (d, J=1.8 Hz, 1H), 3.88 (t, J=5.0 Hz, 4H), 2.47 (t, J=5.1 Hz, 4H), 2.33 (s, 3H), 2.31 (s, 3H), 2.06 (s, 3H).

Example 16

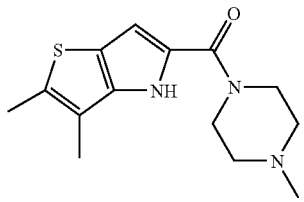

(2,3-Dimethyl-4H-thieno[3,2-b]pyrrol-5-yl)-(4-methyl-piperazin-1-yl)-methanone

A. 2,3-Dimethyl-4H-thieno[3,2-b]pyrrole-5-carboxylic acid ethyl ester. 4,5-Dimethyl-thiophene-2-carbaldehyde (2.0 g, 14 mmol) was annulated according to Procedure A to provide the title compound (160 mg, 5%) as a white solid. TLC (silica, 10% EtOAc/hexanes): R$_f$=0.40. $^1$H NMR (CDCl$_3$, 400 MHz): 9.50 (br s, 1H), 7.05 (d, J=1.9 Hz, 1H), 4.36 (q, J=7.2 Hz, 2H), 2.41 (s, 3H), 2.22, (s, 3H), 1.38 (t, J=7.2 Hz, 3H).

B. (2,3-Dimethyl-4H-thieno[3,2-b]pyrrol-5-yl)-(4-methyl-piperazin-1-yl)-methanone. 2,3-Dimethyl-4H-thieno[3,2-b]pyrrole-5-carboxylic acid ethyl ester (68 mg, 0.30 mmol) was hydrolyzed (Procedure B) and then coupled with N-methylpiperazine (Procedure D) to provide the title compound (67 mg, 80% for two steps) as an off-white solid. TLC (silica, 10% MeOH/CH$_2$Cl$_2$): R$_f$=0.35. MS (electrospray): exact mass calculated for C$_{14}$H$_{19}$N$_3$OS, 277.12; m/z found, 278.1 [M+H]$^+$. $^1$H NMR (CDCl$_3$, 400 MHz): 10.95 (br s, 1H), 6.63 (d, J=1.9 Hz, 1H), 3.92 (t, J=4.5 Hz, 4H), 2.46 (t, J=5.0 Hz, 4H), 2.36 (s, 3H), 2.33 (s, 3H), 2.13 (s, 3H).

Examples 17-25

The following compounds were made according to the synthetic methods outlined in Schemes 1-4:

EX Compound
17 (2,3-Dichloro-6H-thieno[2,3-b]pyrrol-5-yl)-(4-methyl-piperazin-1-yl)-methanone;
18 (2-Methyl-4H-furo[3,2-b]pyrrol-5-yl)-piperazin-1-yl-methanone;
19 (3-Bromo-4H-thieno[3,2-b]pyrrol-5-yl)-piperazin-1-yl-methanone;
20 (3-Bromo-4H-thieno[3,2-b]pyrrol-5-yl)-(3-methyl-piperazin-1-yl)-methanone;
21 (3-Methyl-4H-thieno[3,2-b]pyrrol-5-yl)-piperazin-1-yl-methanone;
22 (3-Methyl-piperazin-1-yl)-(3-methyl-4H-thieno[3,2-b]pyrrol-5-yl)-methanone;
23 (2-Chloro-3-methyl-4H-thieno[3,2-b]pyrrol-5-yl)-(4-methyl-piperazin-1-yl)-methanone;
24 (2-Chloro-3-methyl-4H-thieno[3,2-b]pyrrol-5-yl)-piperazin-1-yl-methanone; and
25 (2,3-Dichloro-4H-thieno[3,2-b]pyrrol-5-yl)-(4-methyl-piperazin-1-yl)-methanone.

Biological Examples

Binding Assay on Recombinant Human Histamine H$_4$ Receptor

SK—N-MC cells or COS7 cells were transiently transfected with pH4R and grown in 150 cm$^2$ tissue culture dishes. Cells were washed with saline solution, scraped with a cell scraper and collected by centrifugation (1000 rpm, 5 min). Cell membranes were prepared by homogenization of the cell pellet in 20 mM Tris-HCl with a polytron tissue homogenizer for 10 s at high speed. Homogenate was centrifuged at 1000 rpm for 5 min at 4° C. The supernatant was then collected and centrifuged at 20,000×g for 25 min at 4° C. The final pellet was resuspended in 50 mM Tris-HCl. Cell membranes were incubated with $^3$H-histamine (5-70 nM) in the presence or absence of excess histamine (10000 nM). Incubation occurred at room temperature for 45 min. Membranes were harvested by rapid filtration over Whatman GF/C filters and washed 4 times with ice-cold 50 mM Tris HCl. Filters were then dried, mixed with scintillant and counted for radioactivity. SK—N-MC or COS7 cells expressing human histamine H$_4$ receptor were used to measure the affinity of binding of other compounds and their ability to displace $^3$H-ligand binding by incubating the above-described reaction in the presence of various concentrations of inhibitor or compound to be tested. For competition binding studies using $^3$H-histamine, K$_i$ values were calculated, based on an experimentally determined K$_D$ value of 5 nM and a ligand concentration of 5 nM, according to Y.-C. Cheng and W. H. Prusoff (*Biochem. Pharmacol.* 1973, 22(23):3099-3108): K$_i$=(IC$_{50}$)/(1+([L]/(K$_D$))).

| BINDING ASSAY RESULTS | |
|---|---|
| EX | K$_i$ (nM) |
| 1 | 85 |
| 2 | 461 |
| 3 | 25 |
| 4 | 176 |
| 5 | 56 |
| 6 | 840 |
| 7 | 125 |
| 8 | 343 |
| 9 | 733 |
| 10 | 40 |
| 11 | 715 |
| 12 | 56 |
| 13 | 21 |
| 14 | 343 |
| 15 | 140 |
| 16 | 5 |
| 17 | 10 |
| 18 | 770 |
| 19 | 410 |
| 20 | 980 |
| 21 | 80 |
| 22 | 161 |
| 23 | 3 |
| 24 | 30 |
| 25 | 5.5 |

Mast Cell Chemotaxis Assay

Mast cell accumulation in mucosal epithelia is a well-known characteristic of allergic rhinitis and asthma. Transwells (Costar, Cambridge, Mass.) of a pore size 8 µm were coated with 100 µL of 100 ng/mL human fibronectin (Sigma) for 2 h at room temperature. After removal of the fibronectin, 600 µL of RPMI with 5% BSA, in the presence of 10 µM histamine, was added to the bottom chamber. To test the various histamine receptor (HR) antagonists, 10 µM and/or 1 µM solutions of the test compounds were added to the top and bottom chambers. Mast cells ($2\times10^5$/well) were added to the top chamber. The plates were incubated for 3 h at 37° C. Transwells were removed and the cells in the bottom chamber were counted for sixty seconds using a flow cytometer.

| | 10 µM Histamine | | | | |
|---|---|---|---|---|---|
| | HR Antagonist (µM): | | | | Binding |
| | 10 | | 1 | | Assay |
| EX | % Inh | Stdev | % Inh | Stdev | $K_i$ (nM) |
| 3 | 106 | 4 | 103 | 0 | 25 |
| 4 | <5 | — | <5 | — | 176 |
| 10 | | | 92 | 3 | 40 |
| 13 | | | 60 | 20 | 21 |
| 20 | <5 | — | <5 | — | 980 |

Cell-Type Distribution of $H_4$ Expression

RNA was prepared from the different cells using an RNeasy kit (Qiagen, Valencia, Calif.) according to the manufacturer's instructions. RNA samples (5 µg) were run on an RNA gel and then transferred overnight to a nylon blot (Hybond, Amersham Pharmacia Biotech, Piscataway, N.J.). The blot was pre-hybridized with ExpressHyb solution (CLONTECH) for 30 min at 68° C. The $H_4$ receptor DNA was labeled using the Rediprime II kit (Amersham Pharmacia Biotech). The blot was hybridized for 2 h at 68° C., followed by one wash step (23 SSC and 0.05% SDS) of 40 min at room temperature, and a second wash step (0.13 SSC and 0.1% SDS) of 40 min at 50° C. The blot was exposed to X-ray film at −70° C. with two intensifying screens overnight.

Results

The Northern Blot results indicate that the $H_4$ receptor is expressed on bone marrow-derived mast cells (BMMC), peritoneal mast cells, and eosinophils. These positive results are consistent with the published literature (e.g. Oda et al., Nguyen et al., and Morse et al. in the Background section). However, the negative results of the Northern Blot experiment, such as the finding of apparently no measurable levels of $H_4$ receptor expressed by neutrophils, differ somewhat from the above literature findings. This may be explained by the different methodologies used. Accumulation of mast cells and eosinophils in affected tissues is one of the principal characteristics of allergic rhinitis and asthma. Since $H_4$ receptor expression is limited to these cell types; $H_4$ receptor signalling is likely to mediate the infiltration of mast cells and eosinophils in response to histamine. Additional investigation may also clarify these issues. The following table reports the Cell-type Distribution of $H_4$ Expression by Northern Blot.

| Species | Cell Type | $H_4$ |
|---|---|---|
| Human | Eosinophils | + |
| | Immature Dendritic Cells | − |
| | Mature Dendritic Cells | − |

-continued

| Species | Cell Type | $H_4$ |
|---|---|---|
| | $CD14^+$ Monocytes | − |
| | $CD4^+$ T Cells | − |
| | $CD8^+$ T Cells | − |
| | B Cells | − |
| | Neutrophils | − |
| Mouse/(Rat) | Eosinophils | + |
| | Peritoneal Mast Cells (Rat) | + |
| | BMMC | + |
| | BM Derived Macrophages | − |
| | Peritoneal Macrophages | − |
| | $CD4^+$ T Cells | − |
| | B Cells | − |

The Inhibition of Eosinophil Shape Change by Histamine $H_4$ Receptor Antagonists Eosinophil accumulation in sites of allergic reaction is a well-known characteristic of allergic rhinitis and asthma. This example demonstrates that histamine $H_4$ receptor antagonists can block the shape change response in human eosinophils in response to histamine. Shape change is a cellular characteristic that precedes eosinophil chemotaxis.

Methods

Human granulocytes were isolated from human blood by a Ficoll gradient. The red blood cells were lysed with 5-10× Qiagen lysis buffer at room temperature for 5-7 min. Granulocytes were harvested and washed once with FACS buffer. The cells were resuspended at a density of $2\times10^6$ cells/mL in reaction buffer. To test inhibition by specific histamine receptor antagonists, 90 µL of the cell suspension (~$2\times10^5$ cells) was incubated with 10 µM of one of the various test compound solutions. After 30 min, 11 µL of one of the various concentrations of histamine was added. Ten minutes later the cells were transferred to ice and fixed with 250 µL of ice-cold fixative buffer (2% formaldehyde) for 1 min. The shape change was quantitated using a gated autofluoescence forward scatter assay (GAFS) (Byran et al., *Am. J. Crit. Care Med.* 2002, 165:1602-1609).

Results—Histamine Mediates Eosinophil Shape Change Through $H_4$ Receptor

The change in shape of eosinophils is due to cytoskeletal changes that preceed chemotaxis and thus is a measure of chemotaxis. The data in the following table show that histamine induces a dose-dependent shape change in eosinophils. Histamine receptor (HR) antagonists were used to sort out which histamine receptor is responsible for the shape change. Antagonists specific for the histamine $H_1$ receptor (diphenhydramine) or the $H_2$ receptor (ranatidine) did not alter the histamine-induced shape change. However, a dual $H_3/H_4$ antagonist (thioperamide) and a specific histamine $H_4$ receptor antagonist ((5-Chloro-1H-indol-2-yl)-(4-methyl-piperazin-1-yl)-methanone, $K_i$=5 nM) inhibited histamine-induced eosinophil shape change with an $IC_{50}$ of 1.5 and 0.27 µM, respectively.

| Histamine | Fold Change | | | | |
|---|---|---|---|---|---|
| (µM): | 10 | 1 | 0.1 | 0.01 | 0 |
| No HR Antagonist | 1.34 | 1.31 | 1.21 | 1.01 | 1.00 |

-continued

| Histamine | Fold Change | | | | |
|---|---|---|---|---|---|
| (μM): | 10 | 1 | 0.1 | 0.01 | 0 |
| 10 μM $H_4$ Antagonist | 1.09 | 1.05 | 1.05 | 1.01 | 1.00 |
| 10 μM Thiop | 1.08 | 1.05 | 1.01 | 1.04 | 1.00 |
| 10 μM Diphen | 1.63 | 1.50 | 1.18 | 1.03 | 1.00 |
| 10 μM Ranat | 1.64 | 1.49 | 1.21 | 1.04 | 1.00 |

The Inhibition of Eosinophil Chemotaxis by Histamine $H_4$ Receptor Antagonists

Eosinophil accumulation in sites of allergic reaction is a well-known characteristic of allergic rhinitis and asthma. Eosinophils are purified from human blood with standard methods. Chemotaxis assays are carried out using transwells (Costar, Cambridge, Mass.) of a pore size 5 μm coated with 100 μL of 100 ng/mL human fibronectin (Sigma) for 2 h at room temperature. After removal of the fibronectin, 600 μL of RPMI with 5% BSA in the presence of histamine (ranging from 1.25-20 μM) is added to the bottom chamber. To test the various histamine receptor antagonists 10 μM of the test compounds can be added to the top and bottom chambers. Eosinophils will be added to the top chamber whereas histamine or chemotactic factors will be placed in the lower chamber. The plates are incubated for 3 h at 37° C. Transwells are removed and the number of cells in the bottom chamber can be counted for 60 s using a flow cytometer, or can be quantitated by using Giemsa staining.

The Inhibition of Zymosan-Induced Peritonitis in Mice by Histamine $H_4$ Receptor Antagonists It has been demonstrated that histamine $H_4$ receptor antagonists can block the peritonitis induced by zymosan, which is the insoluble polysaccharide component on the cell wall of *Saccharomyces cerevisiae*. This is commonly used to induce peritonitis in mice and appears to act in a mast cell-dependent manner. Compounds of the present invention can be tested in such a model to demonstrate their use as anti-inflammatory agents. At time 0 mice are given compound or PBS, either s.c. or p.o. Fifteen minutes later each mouse receives 1 mg zymosan A (Sigma) i.p. The mice are sacrificed 4 h later, and the peritoneal cavities are washed with 3 mL of PBS containing 3 mM EDTA. The number of migrated leukocytes is determined by taking an aliquot (100 μL) of the lavage fluid and diluting 1:10 in Turk's solution (0.01% crystal violet in 3% acetic acid). The samples are then vortexed, and 10 μL of the stained cell solution is placed in a Neubauer haemocytometer. Differential cell counts are performed using a light microscope (Olympus B061). In view of their chromatic characteristics and their nucleus and cytoplasm appearance, polymorphonuclear leukocytes (PMN; >95% neutrophils) can be easily identified. Treatment with zymosan increases the number of neutrophils, which is representative of an inflammatory response. Treatment with $H_4$ receptor antagonist will block this increase.

Inhibition of Mast Cell Chemotaxis by $H_4$ Receptor Antagonist in an Animal Model of Asthma and Allergic Rhinitis An animal model will be used to test the observation that mast cells accumulate in response to allergic inflammation and that this can be blocked by $H_4$ receptor antagonists. Compounds of the present invention can be tested in this model to demonstrate their use as treatments for allergic rhinitis or asthma. Mice will be sensitized by intraperitoneal injection of ovalbumin/Alum (10 μg in 0.2 ml Al(OH)$_3$; 2%) on Day 0 and Day 14. On Day 21 through 23 mice will be challenged by PBS or ovalbumin, and sacrificed 24 h after the last challenge on Day 24. A section of the trachea will be removed and fixed in formalin. Paraffin embedding and longitudinal sectioning of tracheas will be performed followed by staining of mast cells with toluidine blue. Alternatively, trachea will be frozen in OCT for frozen sectioning, and mast cells will be identified by IgE staining. Mast cells will be quantified as sub-mucosal or sub-epithelial depending on their location within each tracheal section. Exposure to allergen should increase the number of sub-epithelial mast cells, and this effect will be blocked by $H_4$ receptor antagonists.

The features and advantages of the invention are apparent to one of ordinary skill in the art. Based on this disclosure, including the summary, detailed description, background, examples, and claims, one of ordinary skill in the art will be able to make modifications and adaptations to various conditions and usages. Publications described herein are incorporated by reference in their entirety. These other embodiments are also within the scope of the invention.

What is claimed is:

1. A compound selected from the group consisting of:
   (4-Methyl-piperazin-1-yl)-(6H-thieno[2,3-b]pyrrol-5-yl)-methanone;
   (Hexahydro-pyrrolo[1,2-a]pyrazin-2-yl)-(6H-thieno[2,3-b]pyrrol-5-yl)-methanone;
   (2-Chloro-6H-thieno[2,3-b]pyrrol-5-yl)-(4-methyl-piperazin-1-yl)-methanone;
   (2-Chloro-6H-thieno[2,3-b]pyrrol-5-yl)-(hexahydro-pyrrolo[1,2-a]pyrazin-2-yl)-methanone;
   (2-Chloro-6H-thieno[2,3-b]pyrrol-5-yl)-piperazin-1-yl-methanone;
   (4-Methyl-piperazin-1-yl)-(4H-thieno[3,2-b]pyrrol-5-yl)-methanone;
   Piperazin-1-yl-(4H-thieno[3,2-b]pyrrol-5-yl)-methanone;
   (3-Methyl-piperazin-1-yl)-(4H-thieno[3,2-b]pyrrol-5-yl)-methanone;
   (2-Chloro-4H-thieno[3,2-b]pyrrol-5-yl)-(4-methyl-piperazin-1-yl)-methanone;
   (2-Chloro-4H-thieno[3,2-b]pyrrol-5-yl)-(hexahydro-pyrrolo[1,2-a]pyrazin-2-yl)-methanone;
   (3-Bromo-4H-thieno[3,2-b]pyrrol-5-yl)-(4-methyl-piperazin-1-yl)-methanone;
   (4-Methyl-piperazin-1-yl)-(3-methyl-4H-thieno[3,2-b]pyrrol-5-yl)-methanone;
   (2,3-Dimethyl-4H-thieno[3,2-b]pyrrol-5-yl)-(4-methyl-piperazin-1-yl)-methanone;
   (2,3-Dichloro-6H-thieno[2,3-b]pyrrol-5-yl)-(4-methyl-piperazin-1-yl)-methanone;
   (3-Bromo-4H-thieno[3,2-b]pyrrol-5-yl)-piperazin-1-yl-methanone;
   (3-Bromo-4H-thieno[3,2-b]pyrrol-5-yl)-(3-methyl-piperazin-1-yl)-methanone;
   (3-Methyl-4H-thieno[3,2-b]pyrrol-5-yl)-piperazin-1-yl-methanone;
   (3-Methyl-piperazin-1-yl)-(3-methyl-4H-thieno[3,2-b]pyrrol-5-yl)-methanone;
   (2-Chloro-3-methyl-4H-thieno[3,2-b]pyrrol-5-yl)-)4-methyl-piperazin-1-yl)-methanone;
   (2-Chloro-3-methyl-4H-thieno[3,2-b]pyrrol-5-yl)-piperazin-1-yl-methanone;
   (2,3-Dichloro-4H-thieno[3,2-b]pyrrol-5-yl)-(4-methyl-piperazin-1-yl)-methanone;

(2,3-Dimethyl-6H-thieno[2,3-b]pyrrol-5-yl)-(4-methyl-piperazin-1-yl)-methanone;
(2-Chloro-3-methyl-6H-thieno[2,3-b]pyrrol-5-yl)-(4-methyl-piperazin-1-yl)-methanone;
(3-Chloro-2-methyl-6H-thieno[2,3-b]pyrrol-5-yl)-(4-methyl-piperazin-1-yl)-methanone;
(2-Bromo-6H-thieno[2,3-b]pyrrol-5-yl)-(4-methyl-piperazin-1-yl)-methanone;
(3-Bromo-6H-thieno[2,3-b]pyrrol-5-yl)-(4-methyl-piperazin-1-yl)-methanone;
(4-Methyl-piperazin-1-yl)-(2-phenyl-6H-thieno[2,3-b]pyrrol-5-yl)-methanone;
[2-(4-Chloro-phenyl)-6H-thieno[2,3-b]pyrrol-5-yl]-(4-methyl-piperazin-1-yl)-methanone;
(3-Bromo-4H-thieno[3,2-b]pyrrol-5-yl)-(3,4-dimethyl-piperazin-1-yl)-methanone;
(3,4-Dimethyl-piperazin-1-yl)-(3-methyl-4H-thieno[3,2-b]pyrrol-5-yl)-methanone;
(2-Bromo-3-methyl-4H-thieno[3,2-b]pyrrol-5-yl)-(4-methyl-piperazin-1-yl)-methanone;
(3-Bromo-2-chloro-4H-thieno[3,2-b]pyrrol-5-yl)-(4-methyl-piperazin-1-yl)-methanone;
(2,3-Dichloro-4H-thieno[3,2-b]pyrrol-5-yl)-(3-methyl-piperazin-1-yl)-methanone;
(4-Methyl-piperazin-1-yl)-(2-phenyl-4H-thieno[3,2-b]pyrrol-5-yl)-methanone; and
(4-Methyl-piperazin-1-yl)-[2-(4-trifluoromethyl-phenyl)-4H-thieno[3,2-b]pyrrol-5-yl]-methanone;
and enantiomers, diastereomers and pharmaceutically acceptable salts thereof.

2. A pharmaceutical composition containing at least one compound of claim 1 and enantiomers, diastereomers and pharmaceutically acceptable salts thereof.

* * * * *

UNITED STATES PATENT AND TRADEMARK OFFICE
CERTIFICATE OF CORRECTION

| | | |
|---|---|---|
| PATENT NO. | : 7,645,758 B2 | Page 1 of 1 |
| APPLICATION NO. | : 11/735306 | |
| DATED | : January 12, 2010 | |
| INVENTOR(S) | : Hui Cai et al. | |

It is certified that error appears in the above-identified patent and that said Letters Patent is hereby corrected as shown below:

On the Title page, item [73]: that portion of the assignee's name reading "N.Y." should be changed to --N.V.--.

Signed and Sealed this

Thirtieth Day of November, 2010

David J. Kappos
*Director of the United States Patent and Trademark Office*